(12) United States Patent
Meyers et al.

(10) Patent No.: US 8,217,368 B2
(45) Date of Patent: Jul. 10, 2012

(54) SYSTEM AND METHOD FOR DETERMINING THREE-DIMENSIONAL INFORMATION FROM PHOTOEMISSION INTENSITY DATA

(76) Inventors: Ronald Everett Meyers, Columbia, MD (US); David Lawrence Rosen, Rockville, MD (US)

( * ) Notice: Subject to any disclaimer, the term of this patent is extended or adjusted under 35 U.S.C. 154(b) by 0 days.

(21) Appl. No.: 12/940,204

(22) Filed: Nov. 5, 2010

(65) Prior Publication Data

US 2012/0112096 A1     May 10, 2012

(51) Int. Cl.
*H01J 65/06* (2006.01)
(52) U.S. Cl. .................................................. 250/459.1
(58) Field of Classification Search ............... 250/459.1, 250/393, 433; 356/448
See application file for complete search history.

(56) References Cited

U.S. PATENT DOCUMENTS

| | | | | |
|---|---|---|---|---|
| 7,003,143 B1* | 2/2006 | Hewitt et al. | ................. | 382/128 |
| 7,116,415 B2* | 10/2006 | Iuliano | ......................... | 356/301 |
| 2009/0086903 A1* | 4/2009 | Boyden et al. | ................. | 378/45 |

OTHER PUBLICATIONS

Nayar, S.K., et al. "Generalization of the Lambertian model and implications for machine vision," International Journal of Computer Vision, vol. 14, pp. 227-251, 1995.
Westlund, Harold B. The Role of Rendering in the Competence Project in Measurement Science for Optical Reflection and Scattering, n. J. Res. Natl. Inst. Stand. Technol. 107, 247-259 (2002).
Alison Rodger and Bengt Norden, "Circular Dichroism and Linear Dichroism" (Oxford, 1997) pp. 45-89.
G.P. Gobbi, F. Barnaba, M. Blumthaler, G. Labow, and J.R. Herman, "Observed effects of particles nonsphericity on retrieval of marine and desert dust aerosol optical depth by lidar," Atmospheric Research 61,1-14 (2002).

Mishchenko, Michael, Scattering, Absorption, and Emission of Light by Small Particles (Cambridge, 2002) pp. 8-30.
Smith, Matthew, et al., "Multispectral infrared Stokes imaging polarimeter" (Proceedings Paper) in Polarization Measurement, Analysis, and Remote Sensing, ed. D. H. Goldstein and D. B. Renault Proceedings of SPIE V. 3754 (1999).
Smith, Matthew, et al., "Beam Wander Considerations in Imaging Polarimetry," in Polarization: Measurement, Analysis, and Remote Sensing II, D. H. Goldstein, D. B. Chenault, eds., Proceedings of SPIE 3754, 50-54 (1999).
Shaw, Joseph, "Degree of linear polarization in spectral radiances from water-viewing infrared radiometers," Appl. Opt. 38(15), 3157-3165 (1999).
Obukhov, A.M., et al. Polarization of the Twilight Sky: Measurements, Empirical Model, Radiative Transfer Simulation and Application to Aerosol Profile Retrieval, II ovp@omega.ifaran.ru. ugol@tanatos.asc.rssi.ru (2003).
Swap, Robert R., "Africa burning: a thematic analysis of Southern African Regional Science Initiative-SAFARI," J. Geophys. Res. submitted (2003).

(Continued)

*Primary Examiner* — David Porta
*Assistant Examiner* — Faye Boosalis
(74) *Attorney, Agent, or Firm* — Lawrence E. Anderson

(57) ABSTRACT

A method and system for investigating properties of an object comprising: a transmitter, including a radiation source, the transmitter providing incident radiation having a plurality of predetermined polarization states; the incident radiation illuminating an object and thereby causing the object to emit photoemission; a receiver, receiving photoemission from the object when the object is illuminated by the incident radiation, the receiver including a detector, the detector providing photoemission intensity data; and signal processing circuitry, in electrical communication with the detector, the signal processing circuitry determining three-dimensional information relating to the object from the photoemission intensity data for each of the plurality of incident polarization states.

21 Claims, 13 Drawing Sheets

OTHER PUBLICATIONS

Shaw, Joseph A. "Polarized infrared emissivity for a rough water surface," Opt. Exp. 7, 25342 (2000).

Acharya, K. et al. "MODTRAN4: Multiple Scattering and Bi-Directional Reflectance Distribution Function (BRDF) Upgrades to MODTRAN," SPIR Proc. 3756,1-9 (1999).

Berk, A. "MODTRAN Radiative transfer modelling for atmospheric correction," JPL Report 1-7 (1999) paper was published in the SPIE Proceeding, Optical Spectroscopic Techniques and Instrumentation for Atmospheric and Space Research III, vol. 3756, Jul. 1999.

Meyers, Jason, "Modeling Polarimetric Imaging using DIRSIG", RIT Imaging Science Ph.D. thesis (Chester F. Carlson Center for Imaging Science Rochester Institute of Technology, 2002).

Kim, A.D. et al. "Influence of the relative refractive index on the depolarization of multiply scattered waves," Physical Review E, vol. 64, 026612 published Jul. 24, 2001.

Lu, S-Y, "Interpretation of Mueller matrices based on polar decomposition," J. Opt. Soc. Am. A/vol. 13, No. 5/May 1996 p. 1106.

Pierre-Yves Gerligand, et al. "Polarimetric images of a cone," Optics Express 420-430 (1999).

Chipman, Russell, "Polarization analysis of Optical Systems," Optical Engineering 28, 090-099 (1989).

Meyers, Jason, P. et al. "Incorporation of polarization into DIRSIG synthetic image generation model," SPIE 4816,132-143 (2002).

Kenneth K. Ellis, "Polarimetric bidirectional reflectance distribution function of glossy coatings," J.Opt.Soc.Am. 13, 1758-1762 (1996).

Karavas, Panagiotis "Validation/Evaluation of Polarization Version of SEARAD," MS thesis (Hellenic Naval Academy, 1999).

Lagarass, Spiridan, Modeled Detection and Recognition Range for a Polarization Filtered FLIR Sensor, (MS thesis, Helenic Naval Academy, 1999).

Yong, Tan C., "An Infrared Model of R/N Point SUR Using EOPACE Data," Report A156163 (Naval Postgraduate School, 1999).

Cooper, W.A., "Infrared polarization measurements of ship signatures and background contrast" (Proceedings Paper) SPIE 2223, 300-309 (1994).

Burton, Robin, et al, "Elastic LADAR Modeling for Synthetic Imaging Applications," SPIE vol. 23, No. 13, pp. 144-155 (2002).

Lentilucci, Emmerr J. et al. "Advances in Wide Area Hyperspectral Image Simulation,"presented at SPIE AeroSense 2003, SPIE vol. 5075-13 (2003).

Arnold, Peter S. "Hyperspectral Simulation of Chemical Weapons Dispersal Patterns in DIRSIG" (Digital Imaging and Remote SensingLab, Rochester Institute of Technology, 2003).

"Nonconventional Exploitation Factors (NEF) Modeling," Computer Graphic Rendering of Material Surfaces,Website http://math.nist.gov/~FHunt/appearance/nefds.html (est. 2003).

Merino, Oscar Gonzalez "Image analysis of Infrared Polarization measurements of landmines," (VRIJE Universiteit Brussel, Universitat Politecnica, De Catalunya)(Masters Thesis 2001).

Rogne, Timothy J. "Passive Target Detection using Polarized Components of Infrared Signatures," SPIE 1317, 242-251(1990).

Sadjadi, Firooz A. Application of a Passive Polarimetric Infrared Sensor in Improved Detection and Classification of Targets, II International Journal of Infrared and Millimeter Waves 19, 1541-1559 (1998).

Sadjadi, Firooz A. "Automatic target recognition using polarization-sensitive thermal imaging," Proc. SPIE 2485, 353 (1995); doi:10.1117/12.213102.

Chun, C.S. "Polarization-Sensitive Thermal Imaging Sensors for Target Discrimination," SPIE 3375, 326-336 (1998).

W. de Jong, et al. "Usage of polarization features of landmines for improved automatic detection," Proc. SPIE 4038, 241-252 (2000).

Cremer, Frank "Infrared polarization measurements and modeling applied to surface-laid antipersonnel landmines," Opt. Eng. 41, 1021 (2002); doi:10.1117/1.1467362.

Schechner, Yoav Y."Polarization-based vision through haze," AppL Opt. vol. 42, No. 3, 511-525 (Jan. 20, 2003).

Schmitt, J.M. "Use of polarized light to discriminate short-path photons in a multiply scattering medium," AppL Opt. 31 (#30) 6535-6546 (Oct. 20, 1992).

Tooley, Richard D. "Man-made detection using infrared polarization," SPIE 1166, 52-58 (1989).

Westlund Harold B, et al. "A BRDF Database Employing the BeardMaxwell Reflection Model," (University of Oregon) accessed Jul. 21, 2003).

Koenderink, J..J. "Bidirectional reflection distribution function expressed in terms of surface scattering modes," ECCV '96. 4th European Conference on Computer Vision Proceedings, vol. 2, pp. 28-39.

Priest, Richard G. et al., "Polarimetric BRDF in the Microfacet Model," Proceedings of the 2000 Meeting of the Military Sensing Symposia Specialty Group on Passive Sensors: Theory and Measurements,I, 169-181 (2000).

Kato, Seiji et al. "A Comparison of Modeled and Measured Surface Shortwave Irradiance for a Molecular Atmosphere", J. Quant. Spectrosc. Radiat. Transfer Vo!' 61, 493-502 (1999).

Smith, Warren J. "Modern Optical Engineering" ed. 3 (McGraw-Hill, 2000) p. 200.

Germer, Thomas, et al. "Modeling the appearance of special effect pigment coatings," SPIE 4447, 77-86 (2001).

Vosilla, John ,"Northrop Grumman's E-2C Marks Successful First Live-Fire Test of Ballistic Missile Sensor," Northrop Grumman Press Release (Aug. 20, 2001).

Ackenhusen, L. "Infrared/Hyperspectral Methods" [for Landmine Detection}, in Alternatives for Landmine Detection (White House Office of Science and Technology Policy and Rand Science and Technology Policy Institute, to appear Mar. 2003)pp. III-125.

Hackwell, J.A., et al. "LWIR/MWIR Imaging Hyperspectral Sensor for Airborne and Ground-Based Remote Sensing," SPIE Proceedings, vol. 2819, 1996.

Lacombe, "Environmental Influences of Thermal Signatures of Buried Land Mines," U.S. Army, Fact Sheet, Apr. 1999.

Hoffmann, A., et al. "Ground-based lidar measurements from Ny-A° lesund during ASTAR 2007: a statistical overview," Atmos. Chem. Phys. Discuss. 9, 15453-15510, (2009).www.atmos-chem-phys-discuss.net/9/15453/2009/.

Miyazaki et al., "Determining surface orientations of transparent objects based on polarization degrees in visible and infrared wavelengths,"vol. 19, No. 4/J. Opt. Soc. Am. A p. 687-694 (Apr. 2002).

Cremer, et al., "Infrared polarisation measurements of surface and buried anti-personnel landmines,"Proceedings of SPIE vol. 4394, p. 164-175 (2001).

Diner, D., et al., "Multi-angle Imaging SpectroRadiometer (MISR) Instrument Description and Experiment Overview," IEEE Transactions on Geoscienceand Remote Sensing, 36(#4) 1072-1087 (Jul. 1998).

Fatale, et al., "New Initiatives in Natural Environmental Characterization for the Objective Force," United States Military Academy, 1-2 (Sep. 4, 2003).

Horn, et al., "Determining Optical Flow" MIT Artificial Intelligence Laboratory Memo, 572, 1-27 (1980).

McKinley, C., "When the Enemy Has Our Eyes," School of Advanced Power Studies (Jun. 1996).

Narasimhan et al. "Contrast Restoration of Weather Degraded Images" IEEE Transactions on Pattern Analysis and Machine Intelligence, vol. 25, 713-724, 2003.

Preetham et al. "A Practical Analytic Model for Daylight. Computer Graphics" Proceedings of SIGGRAPH 1999, 91-100 (Aug. 1999).

Preetham "Modeling Skylight and Aerial Perspective" www.atLcomJdeveperlSfGGRAPH03f PreethamSig2003CourseNotes.pdf. accessed Sep. 5, 2003.

Siegal et af. "Just Enough Reality: Comfortable 3-D Viewing via Microstereopsis" IEEE Transactions on Circuits and Systems for Video Technology 10(3), 387-396 (Apr. 2000).

Jose' R. A. Torrea~o and Joa~o L. Fernandes "Matching photometric-stereo images" J. Opt. Soc. Am. A/ vol. 15, No. 12/ -p. 2966-2975 (Dec. 1998).

Jose' R. A. Torrea~o, "Natural Photometric Stereo?" Anais do IX SIBGRAPI, outubro de 1996.

Yu, Yizhou, et al. "Recovering Photometric Properties of Architectural Scenes From Photographs," SIGGRAPH '98 Proceedings of the 25th annual conference on Computer graphics and interactive techniques ACM New York, NY, USA © 1998 ISBN:0-89791-999-8 doi>10.1145/280814.280874 pp. 207-217 (1998).

Gian Paolo Gobbi, et al.,"Altitude-resolved properties of a Saharan dust event over the Mediterranean," Atmospheric Environment 34, 5119-5127 (2000).

M. A. Jones and P. W. Bohn, "Total Internal Reflection Fluorescence and Electrocapillary Investigations of Adsorption at the Water-Dichloroethane Electrochemical Interface: Fluorescence-Detected Linear Dichroism Investigation of Adsorption-Driven Reorientation of Di-N-butylaminonaphthylethenylpyridiniumpropylsulfonate," J. Phys. Chem. B 105, 2197-2204 (2001).

Paul L. Edmiston, et al., "Dipole Orientation Distributions in Langmuir-Blodgett Films by Planar Waveguide Linear Dichroism and Fluorescence Anisotropy," J. Phys. Chem. 100,775-7784 (1996).

Lee. R. Moyer, "Counter Concealed Target Technologies," DARPATech2000 (Sep. 6-S, 2000 )www.darpa.mil/darpatech2000 IPresentations ISPO-pdfl 4MoyerCCTB& W. pdf.

Tianshu Liu, "Geometric, Kinematic and Radiometric Aspects of Image-Based Measurement," AIAA 2002-3239, (22nd AIAA Aerodynamic Measurement Technology and Ground Testing Conference Jun. 24-26, 2002) p. 16.

Michael I. Mishchenko, Larry D. Travis, Andrew A. Lads, Scattering, Absorption, and Emission of Light by Small Particles (Cambridge, 2002) p. 100.

Matt Young, Optics and Lasers (Springer, 1977) pp. 43-72.

John David Jackson, Classical Electrodynamics 3rd Ed. (Wiley, 1999) pp. 305-306.

Grant R. Fowles, "Introduction to Modern Optics," 2nd Ed. (Holt, Rheinhart, and Winston, 1975) pp. 43-46.

Driscoll, W.G., Handbook of Optics, McGraw-Hill Book Co., (1978) pp. 14-1, 14-2, 14-39, 14-52 to 14-58, and 15-1 to 15-9.

Michael J. Rigo, Hyperspectral Polarimetry for Satellite Remote Sensing, United States Naval Academy Thesis (1998) (Abstract only).

Ellias, T. et al. "Exploring the Potential of Combining Column Integrated Atmospheric Polarization with Airborne in situ size Distribution Measurements for the Retrieval of an Aerosol Model: a Case Study of a Biomass Burning Plume during SARARI 2000." J. Geophys. Res., vol. 108 No. D13 Date: Jul. 16, 2003 pp. SAF44-1-16.

Coulson, Kinsell L., Polarization and Intensity of Light in the Atmosphere (A. Deepak Publishing, Hampton, VA 1988) pp. 272-291.

Unmanned Aerial Vehicle Roadmap 2000-2025, Office of the Secretary of Defense, dated Apr. 2001, pp. 26-29.

Koenderink, Jan J., "Bidirectional Reflection Distribution Function Expressed in Terms of Surface Scattering Modes," ECCV '96. 4th European Conference on Computer Vision Proceedings, vol. 2, p. 28-39 (1996).

Mishchenko, M., et al., "Light Scattering by Nonspherical Particles, Theory, Measurements and Applications" Academic Press, 2000, pp. 393-416.

Baertlein, B. "Infrared/Hyperspectral Methods" (Paper I) RAND Report MR1608, Ohio State University p. 93-110 (2003) www.rand.org/publications/MR/MR1608/MR1608.appc.pdf.

A. Rogalski and K. Chrzanowski, "Infrared Devices and Techniques" Infrared Handbook of Optoelectronics (Two-Volume Set) Edited by Robert G . W . Brown and John P Dakin Taylor & Francis 2006 pp. 653-692.

Saleh, B.E. Fundamentals of Photonics (Wiley, 1991) p. 205.

John David Jackson, Classical Electrodynamics 3rd Ed. (Wiley, 1999) pp. 300-306.

Lee, Raymond "Digital imaging of clear-sky polarization," Appl. Opt. 37, 1465-1476 (1998).

Howe, James D "Polarization sensing for target acquisition and mine detection," SPIE 4133, 202-213 (2000).

Miyazaki, D., et al. "Transparent Surface Modeling form a Pair of Polarization Images," IEEE Transactions on Pattern Analysis and Machine Intelligence, vol. 26, No. 1, Jan. 2004., pp. 783-782.

* cited by examiner

FIG. 5 Two Types of Polarimetric Imaging: Direct and Fluorescence Detection

FIG. 6 DIFFERENCE BETWEEN REFLECTANCES AT TWO POLARIZATIONS (s and p)

FIG. 7 DEGREE OF POLARIZATION AS A FUNCTION OF INCIDENT ANGLE BY REFLECTANCE OF s AND p POLARIZATION STATES

FIG. 9 DEPOLARIZATION COEFFICIENT (km$^{-1}$) ON DIFFERENT DAYS DURING EXPERIMENT USED IN DEPOLARIZATION COEFFICIENT TABLE. THE ARROWS SHOW BOTH THE SAMPLES AVERAGED AND THE AVERAGE VALUE OF DEPOLARIZATION COEFFICIENT FOR SPHERICAL AND NONSPHERICAL PARTICLES.

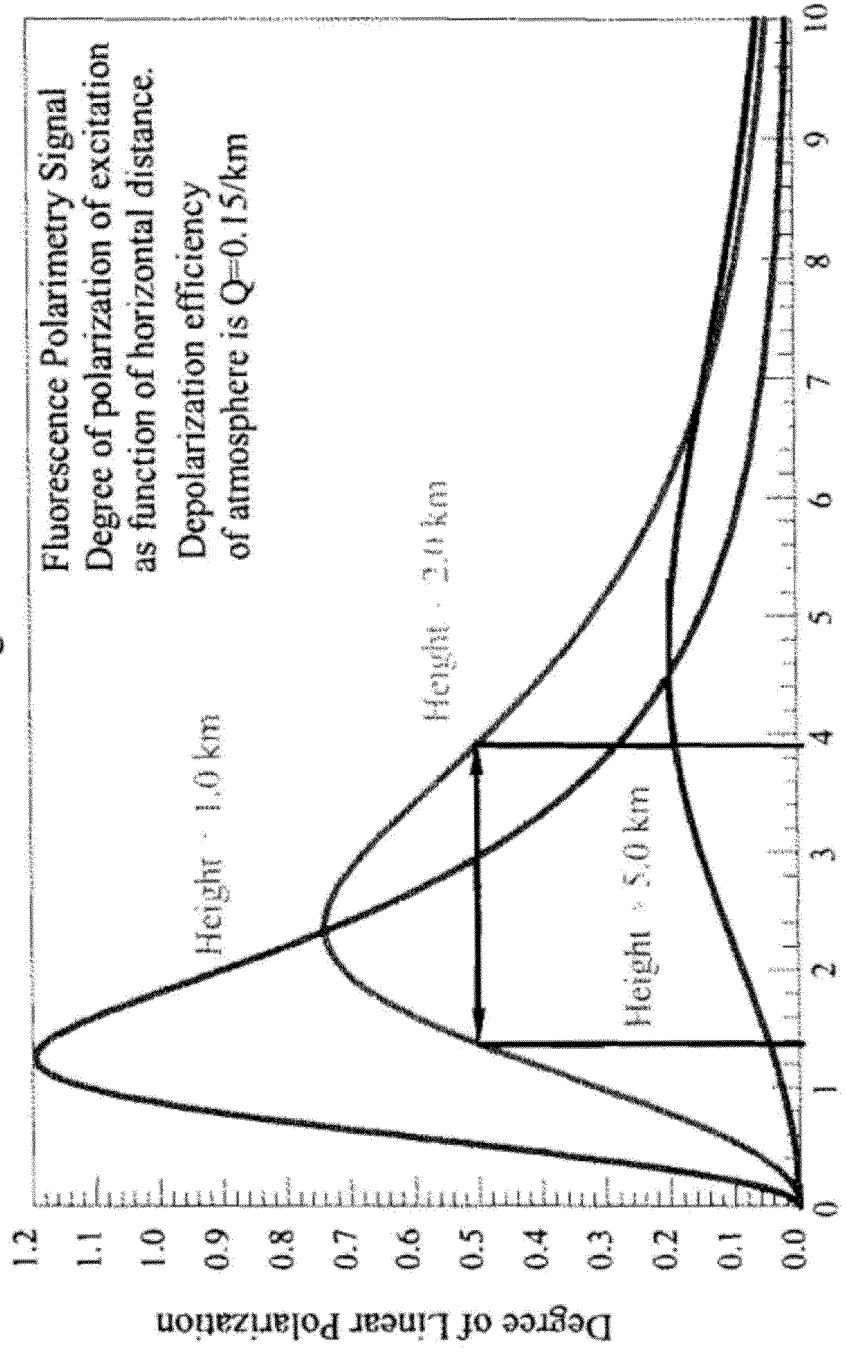
FIG. 10 PREDICTED DEGREE OF LINEAR POLARIZATION P AS A FUNCTION OF DISTANCE FOR THE DUST STORM DESCRIBED WITH q=0.15/km, MEASURED AT THE PEAK OF THE DUST STORM

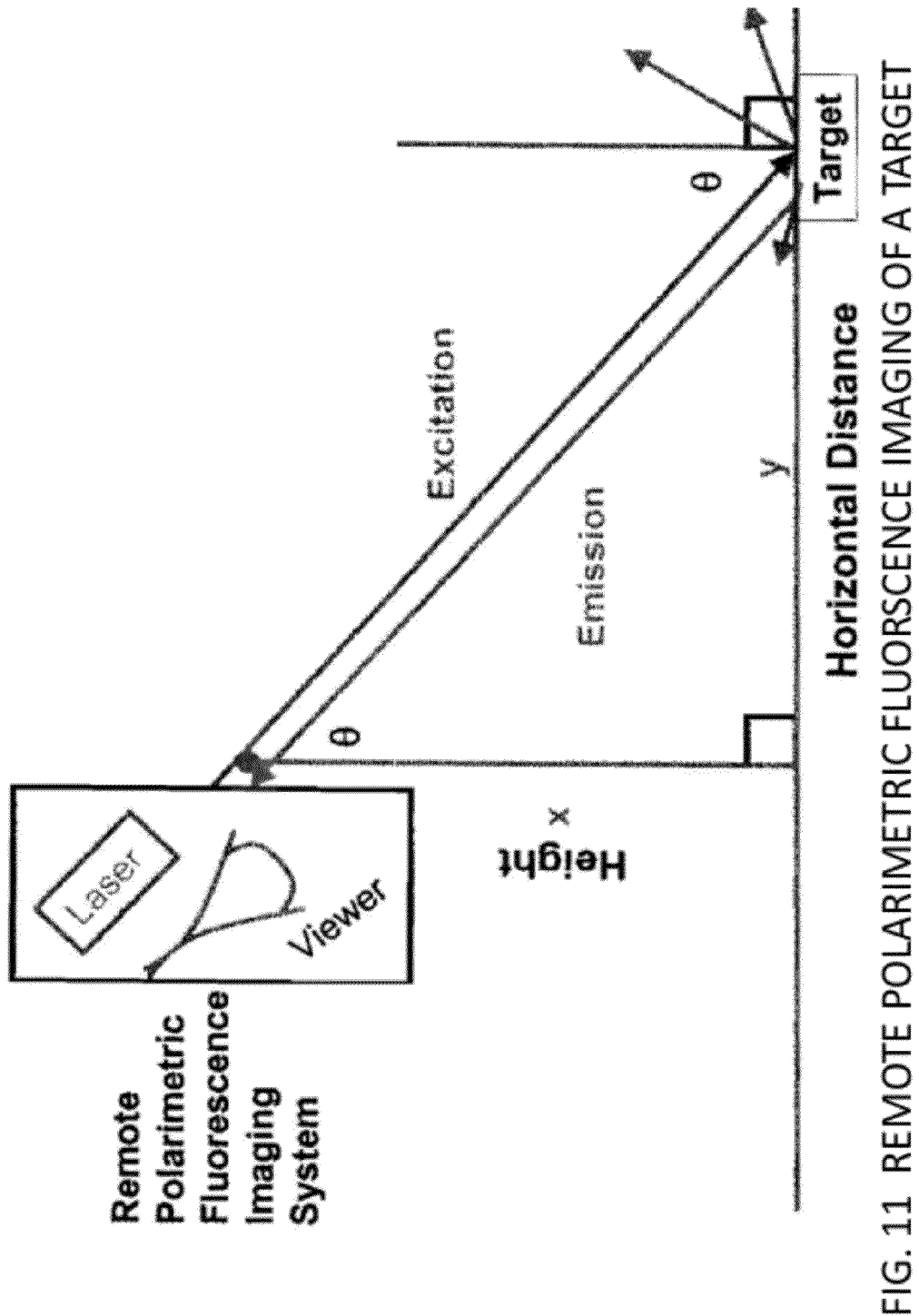
FIG. 11 REMOTE POLARIMETRIC FLUORSCENCE IMAGING OF A TARGET

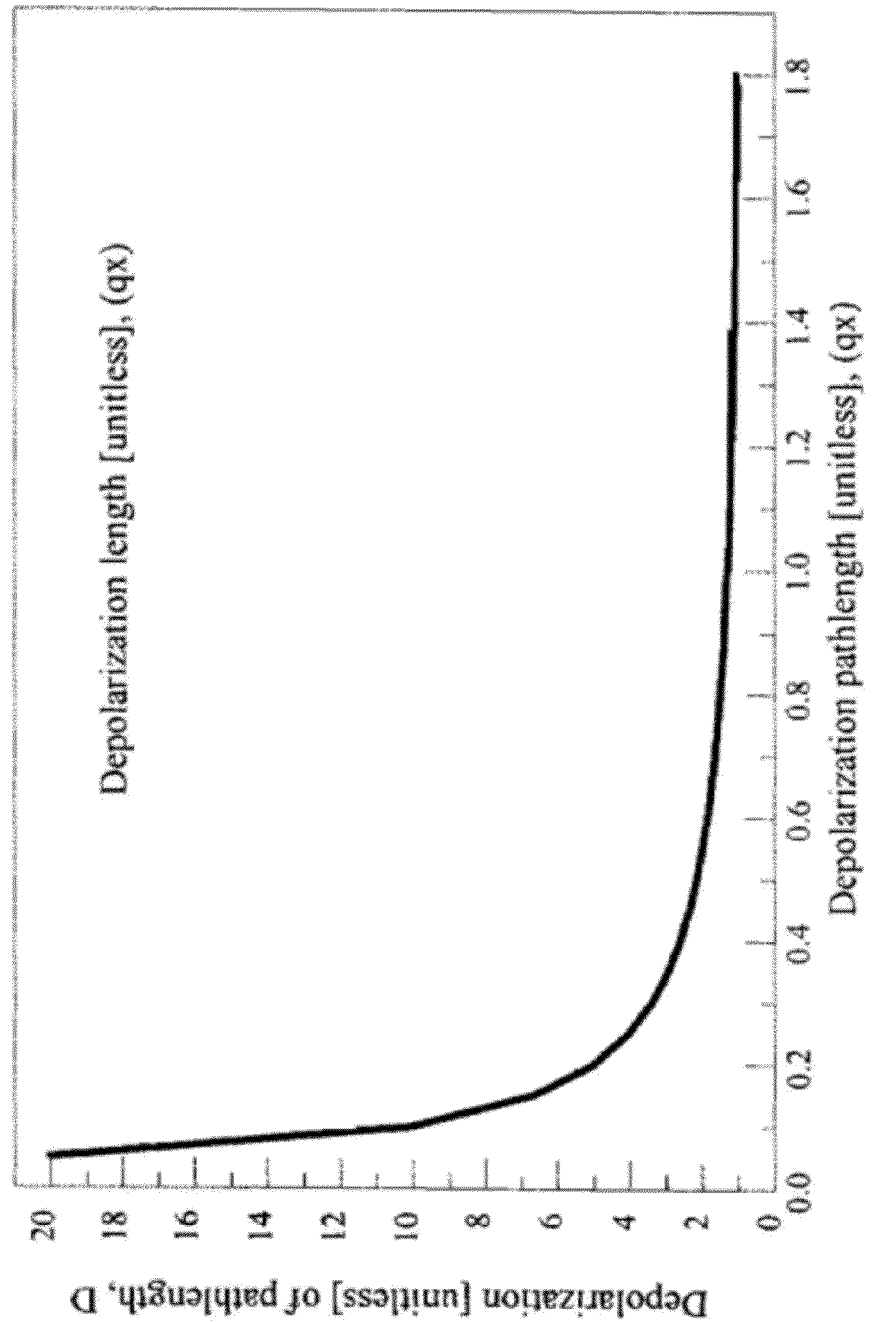
FIG. 12 DEPOLARIZATION COEFFICIENT D AS A FUNCTION OF DISTANCE TIME DEPOLARIZATION STRENGTH, $qx$

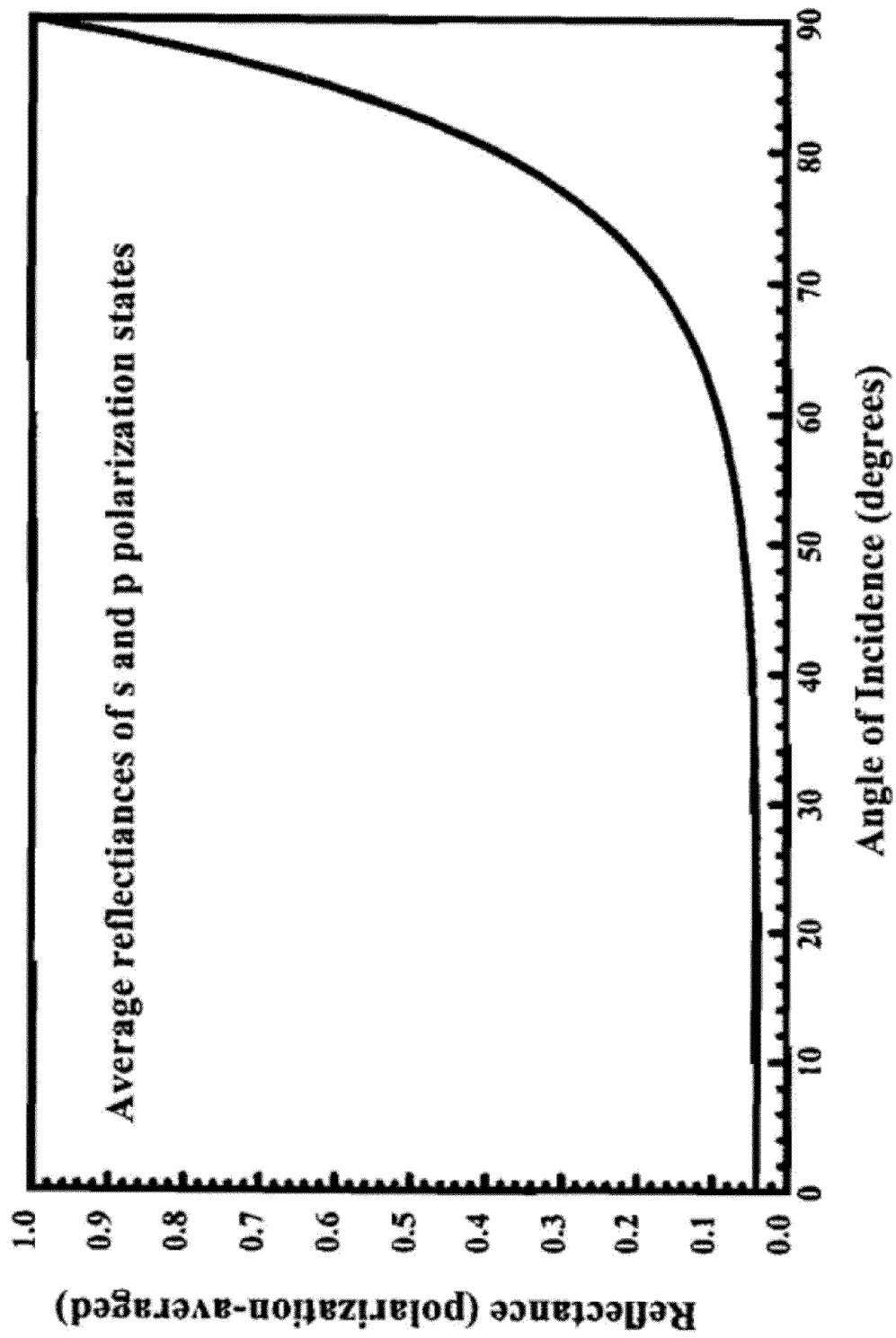
FIG. 13 POLARIZATION-AVERAGED REFLECTANCE

SYSTEM AND METHOD FOR DETERMINING THREE-DIMENSIONAL INFORMATION FROM PHOTOEMISSION INTENSITY DATA

GOVERNMENT INTEREST

The invention described herein may be manufactured, used, and licensed by or for the United States Government.

CROSS REFERENCE TO RELATED APPLICATIONS

This application is related to application Ser. No. 12/940,240 entitled "SYSTEM AND METHOD FOR DETERMINING THREE-DIMENSIONAL INFORMATION FROM TWO-DIMENSIONAL IMAGES," invented by Ronald Meyers, David Rosen, and Keith Deacon, and application Ser. No. 12/940,228 entitled "SYSTEM AND METHOD FOR MEASURING DEPOLARIZATION," invented by David Rosen and Ronald Meyers, both of which are filed on even date herewith and hereby incorporated by reference.

FIELD OF THE INVENTION

The present invention is a method for monocular three-dimensional imaging using the dependence of photoemission (i.e., fluorescence, Raman scattering, or phosphorescence) on the polarization of the illuminating radiation.

BACKGROUND OF THE INVENTION

Techniques for 3-D modeling of objects through observation have been extensively investigated. Such 3-D modeling has a wide range of applications including virtual reality and object recognition. Three-dimensional (stereo) imaging of surfaces by reflected light have been studied performed by several methods, as illustrated in FIG. 5. Binocular stereo imaging is an old, established technique. In binocular imaging, two sets of two-dimensional information (e.g., two-dimensional images) from the surface measured from two different viewpoints at a distance apart.

Another technique illustrated in FIG. 5 is polarimetric stereo imaging. Polarimetry is the measurement and interpretation of the polarization of transverse waves; generally electromagnetic waves, such as radio or light waves. Polarimetry may be done on electromagnetic waves that have traveled through or have been reflected, refracted, or diffracted by some material in order to characterize that object.

Photometric stereo imaging by reflected light has been studied, for example by J. R. A. Torreão and J. L. Fernandes, "Matching photometric-stereo images", *J. Opt. Soc. Am. A* 15 (12), 2966-2975 (1998). Photometric stereo imaging of reflected light uses more than one two-dimensional set of information, measured using reflected light with a wavelength spectrum that varies with the direction of transmitter or receiver. One such transmitter is solar radiation scattered by the atmosphere on a clear day. Another method, using polarimetric reflectance, has also been used for stereo imaging. In polarimetric reflectance, stereo information is determined from sequential measurements of reflectance at different polarization for transmitter or receiver.

Various articles have been written on the spatial arrangement of objects and depth perception. In the publication by B. K. P. Horn and B. G. Schunk, "Determining Optical Flow", MIT Artificial Intelligence Laboratory, 572, 0-27 (1980), hereby incorporated by reference, there is a description of a method for finding optical flow. Optical flow is defined in the article as:

Optical flow is the distribution of apparent velocities of movement of brightness patterns in an image. Optical flow can arise from relative motion of objects and the viewer [citation omitted]. Consequently, optical flow can give important information about the spatial arrangement of the objects viewed and the rate of change of this arrangement [citation omitted]. Discontinuities in the optical flow can help in segmenting images into regions that correspond to different objects.

According to the "Determining Optical Flow" article, in general optical flow cannot be computed locally, since only one independent measurement is available from the image sequence at a point, while the flow velocity has two components. A second constraint is needed. A method for finding the optical flow pattern is presented in the "Determining Optical Flow" article which assumes that the apparent velocity of the brightness pattern varies smoothly almost everywhere in the image. An iterative implementation is shown which successfully computes the optical flow for a number of synthetic image sequences. The algorithm used in "Determining Optical Flow" article reportedly can handle image sequences that are quantized rather coarsely in space and time and is, reportedly, insensitive to quantization of brightness levels and additive noise. Examples are included where the assumption of smoothness is violated at singular points or along lines in the image.

As used herein, the terminology "optical flow" encompasses taking an image of the same scene using different polarizations such that there is an apparent change of intensity from one image to another, such that a vector or vectors may be used to show the apparent movement, which is a representation of the optical flow.

These methods of stereo imaging with reflected radiation have limitations in practice. Reflected radiation contains little information on chemical composition of the surface, regardless of stereo information. Photoemission spectra have long been used to partially determine chemical composition of a surface. Binocular stereo cannot extract three-dimensional information for large distances. Photometric stereo requires the source of illumination to arrive at the surface from more than one direction, each direction having a different wavelength spectrum. Therefore, photometric stereo imaging with reflectance does not function when there is no transmitter available with a spectrum that varies with angle. For example, photometric stereo imaging with solar radiation cannot be used either at noon or on severely overcast days to determine stereoscopic information. Furthermore, the spectroscopic and stereoscopic information cannot be simultaneously extracted with photometric reflectance stereo imaging.

Polarimetric reflectance can be used to extract some three-dimensional information from a surface, e.g. D. Miyazaki et al., "Determining surface orientations of transparent objects based on polarization degrees in visible and infrared wavelengths," *J. Opt. Soc. Am. A* 19, 687-694 (2004). The polarization state, emitted by the transmitter or sensed by the receiver, is varied with time. The variations in signal intensity are also measured at various times and correlated with polarization. However, a unique three-dimensional image by specular reflected radiation cannot be uniquely determined with polarimetric reflectance. A method using two different receiver angles for the illuminating radiation in addition to changing polarization has been developed, but has some of the same problems as binocular reflectance imaging. See D.

Miyazaki et al., "Transparent Surface Modeling from a Pair of Polarization Images," *IEEE Trans. Patt. Anal. Mach. Intel.* 26, 73-82 (2004).

Thus, there exists a need for a remote sensing method of monocular (i.e., single view) stereo imaging without a uniqueness problem for stereo images, yet with a partial chemical selectivity. A method of monocular stereo imaging could have greater effective range for determining the unique three-dimensional shape of a surface than a binocular stereo method, and would be simpler with respect to detection aperture.

SUMMARY OF THE INVENTION

A method and apparatus for monocular polarimetric photoemission is provided to determine the unique three-dimensional structure of a surface using the photoexcited emission with time-varying polarization states of the illuminating radiation.

Monocular polarimetric photoemission is different from other methods currently used for stereoscopic vision. Because one can simultaneously determine a photoemission spectrum which has chemical selectivity, monocular polarimetric photoemission is also different from the other methods using reflectance because photoemission permits a wavelength selective filter to block specular reflected radiation. The method of monocular polarimetric photoemission is different from binocular stereoscopic vision in that the method requires only one viewpoint to determine a stereo image. Polarimetric photoemission is different from photometric stereo imaging in that it can be accomplished with only one wavelength. Therefore, monocular polarimetric photoemission can determine more information than stereoscopic vision methods and with less operational complexity than conventional stereoscopic vision methods.

Novel methods according to embodiments of the present invention include the use of photoemission (i.e., fluorescence, phosphorescence, or Raman) to determine stereoscopic image information, and the measurement of photoemission radiances at different degrees of laser-polarization to determine surface structure.

BRIEF DESCRIPTION OF THE DRAWINGS

FIG. 9 is a graphical illustration of depolarization coefficient ($km^{-1}$) on different days during experiment used in depolarization coefficient table (arrows show both the samples averaged and the average value of the depolarization coefficient for spherical and nonspherical particles;

FIG. 10 is a graphical illustration depicting the predicted degree of linear polarization P as a function of distance for the dust storm scenario described with q=0.15/km, measured at the peak of the dust storm;

FIG. 11 is a diagrammatic illustration of remote polarimetric fluorescence imaging of target;

FIG. 12 is a graphical illustration of depolarization coefficient D as a function of distance time depolarization strength, qx;

FIG. 13 is a graphical illustration of polarization-averaged reflectance.

DESCRIPTION OF THE PREFERRED EMBODIMENTS

The present invention has utility as an object imaging methodology to provide stereoscopic vision information for a single viewing point. In a method according to the present invention, a source of electromagnetic radiation with time-varying differential-polarization provides incident radiation to illuminate an object. Photoemission is emitted from the object, and time variations in photoemission intensity are used to form an image of the object. The possible types of photoemission include fluorescence, phosphorescence, and Raman scattering. The time variations in photoemission intensity with source polarization allow stereo vision information to be determined for the object, and the photoemission intensity as a function of time is used to calculate a surface-height profile of the object from a single viewpoint. The possible types of stereoscopic vision information so provided include a three-dimensional image of the object, or the surface normal direction at the single viewing point to the object.

Stereoscopic vision information is determined from object photoemission measured from any monocular method. With the exception of surface effects, photoemission in a form of fluorescence, phosphorescence, or Raman scatter is almost entirely unpolarized and independent of the polarization of the incident radiation illuminating the object.

Figure 1:
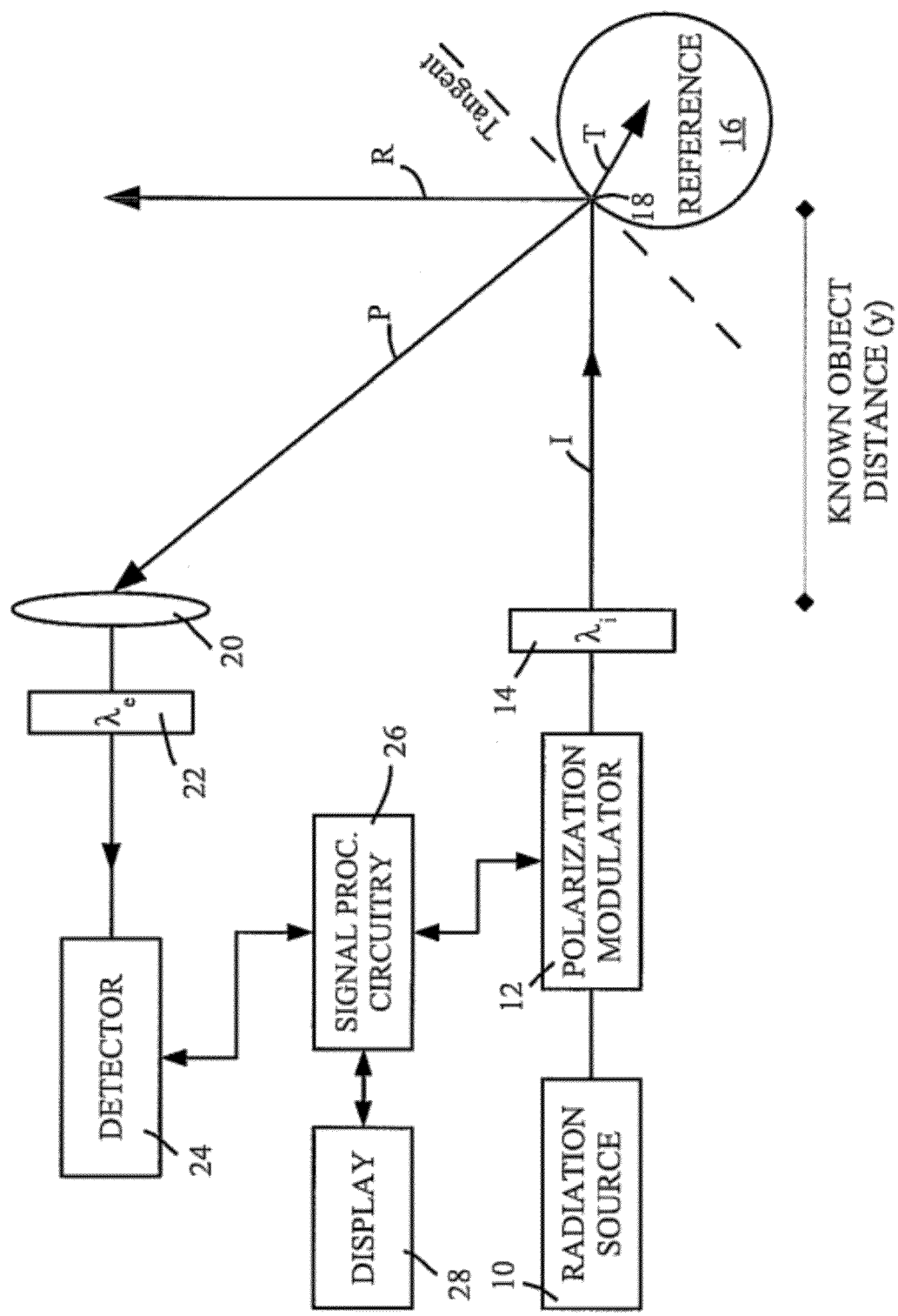
FIG. 1 shows a schematic of an inventive apparatus for remote polarimetric photoemission imaging.

FIG. 1 shows a schematic of an inventive apparatus for remote polarimetric photoemission and spectroscopy using one polarization modulator and a spatial receiver, in this case a camera. The apparatus has a radiation source 10, a polarization modulator 12, and an excitation wavelength filter 14. The filter 14 is a narrow band filter at an excitation wavelength $\lambda_i$ reference. A beam of incident radiation (I) is incident on the surface of an object 16, at point of incidence 18 after passing through a known object distance (y) between the object reference 16 and the filter 14. FIG. 1 shows a tangent (T) to the surface at the point of incidence 18 as a dashed line. A specular reflection beam is produced, labeled R. P is the path of the emitted photoemission radiation, and the reference is the object being probed. A portion of the incident energy is transmitted into the object, as transmitted beam T, where it excites the photoemission. The photoemission (P) is collected by collection lens 20, and passes through an emission wavelength filter 22 to a detector 24. The filter 22 is a narrow band filter at an emission wavelength $\lambda_e$. In this example, the detector is a camera. The signal processing circuitry 26 allows correlation of the detected photoemission intensity with the initial polarization state, and determines the three-dimensional data relating to the object from photoemission intensity data received from the receiver. Three-dimensional data and/or spectral data may be displayed on display 28.

Photoexcited emission, including photoemission and Raman, is commonly used to extract two-dimensional spectroscopic information from an object. However, an embodiment of the present invention utilizes three-dimensional information extracted from such monocular photoexcited-emission images.

The following component descriptions are relevant to the requirements of an inventive apparatus as detailed with respect to the following figures with respect to various reference numerals.

The radiation source provides incident radiation having desired properties for stereo image construction and/or compositional object monocular imaging. The radiation source transmitter has at least one radiation source, such as a laser, and optionally has additional components to modify the properties of the incident radiation, such as one or more lenses, an aperture, a polarizer or polarization modulator, a filter, and the like. The radiation source also optionally includes beam steering components to select an illuminated location on an object.

The incident wavelength may be varied, for example by selecting one of a plurality of radiation sources, tuning a radiation source (such as a dye laser or wavelength adjustable semiconductor laser), or modifying or changing a filter.

The radiation source may be a directional source of electromagnetic radiation such as a laser, or a less directional source such as a collimated arc lamp. The laser radiation is inherently polarized, or alternatively is polarized by an external polarizer. The laser radiation polarization may be controllable by electrical signals applied to the laser, for example applied to an electrooptic material within the laser structure. Electrical signals are applied to a laser, such as a semiconductor laser structure, to control polarization and/or emission wavelength.

The wavelength of the radiation source may be tunable, or one or more of a plurality of radiation sources selected. The incident wavelength may be visible, near-IR, IR, or other electromagnetic range. Many potential applications would use fluorescence excited at UV wavelengths.

A polarization modulator may be an electrooptic modulator, which may contain an electrooptic crystal or a spinning polarization filter. In other examples, the function of a polarization modulator is included in a polarization-varying laser. For example, a polarization-agile semiconductor laser is optionally used instead of an electrooptical modulator.

Detector (Synonymously Spectrometer or Receiver)

The detector includes a collector for photoemission (P) and any associated components, such as a lens or filter, are used to collect and detect the returned radiation.

Returned radiation from the object, such as photoemission or diffuse reflection, is collected by the receiver. The receiver is sensitive to at least one spectrum of visible wavelengths, IR wavelengths (including near-IR and thermal radiation wavelengths), THz, GHz, or other electromagnetic radiation ranges. For example, the receiver is sensitive to near-IR wavelengths and visible, or UV-visible ranges. It is appreciated that many potential applications involve fluorescence emission at visible wavelengths.

It is appreciated that the returned radiation also is optionally Raman scattering. Holographic filters in the receiver are used to selectively transmit Raman scattered radiation.

Signal Processing Circuitry

Apparatus according to the present invention preferably includes signal processing circuitry operational to determine the depolarization efficiency of the radiation transmission medium. The signal processing circuitry allows the receiver signal to be correlated with the polarization modulator, if used, or equivalently the polarization output of the radiation source if this is controllable. A computer provides the functionality of the signal processing circuitry. The computer includes a processor, clock, memory, data input, and data output (such as a display driver, or transmitter in communication with a network). The processor executes one or more algorithms to provide the results of calculations described herein. One additional advantage of photoemission over reflectance is that the signal from specular reflected radiation (i.e., glare) does not have to be analyzed by the signal processing circuit.

Object Reference Location

An object reference to be imaged according to the present invention is located within a medium, such as the air atmosphere. It is appreciated that the present invention is readily used to characterize an object within various media, such as other gases; liquids (such as water, including river water and sea water); and solids, such as glasses.

Object Identification

Surface height profiles of the surface of an object are determined using polarimetric photoemission with a camera receiver. If the receiver is not a camera, partial stereoscopic vision information from the surface is readily determined. For example, the direction and distance of the surface normal is still determined absent a camera. Spectroscopic compositional information is also determined independently or simultaneously, with three-dimensional object stereo image information.

Examples of the present invention also include methods of detecting camouflaged objects, for example by recognizing three-dimensional shapes. Other applications include those in which a surface chemical constitution and/or three-dimensional shape are used for object detection.

Photoemission spectra, both the excitation and the emission spectrum, contain chemical information on the composition of points on the object reference. For example, not all chemical compositions emit photoluminescence. The composition of the three-dimensional surface is determined using previously known spectroscopic methods, such as comparison to a spectral library. Unlike any previously described method, three-dimensional information can be extracted in addition to information on the chemical composition. The ability to chemically identify a remote object affords the ability to detect a decoy variant of an object reference.

The difference between photoemission intensities at the two incident radiation polarizations varies between one angle of incidence and another. The polarimetric photoemission signal includes time variations in emission intensity. The difference in photoemission intensities at two polarization states divided by the polarization-averaged photoemission intensity is designated the degree of polarization of the polarimetric photoemission signal. This differs from the degree of polarization of emitted photoemission, which describes the polarization of emitted radiation.

The specular reflectance, R, of the object varies with the polarization of the incident radiation, I. The energy that is removed by specular reflection is not available to become photoemission emission. Hence, the emission intensity, P, is anti-correlated with the specular reflectance due to radiative transfer, related to the conservation of energy. Therefore, even if the total intensity of incident radiation is constant in time, this intensity of emission may vary with the polarization of the incident radiation. Both stereoscopic and spectral information may be measured independently or simultaneously.

The object reference photoemission carries information on the three-dimensional shape of the object because specular reflectance varies with incident angle as well as incident polarization. Surface curvature and changes in angle of incidence are thus embedded in the object photoemission signal as the time variation of emission intensity.

The emission intensity of object photoemission varies with the linear polarization state of the incident radiation. For example, the Fresnel equations govern the specular reflectance of dielectric materials. The equations indicate that in a dielectric material, the reflectance of s-polarized radiation is greater than reflectance of p-polarized radiation.

The present invention is operative to extract both three-dimensional information from an object surface, independent from, or simultaneous with spectroscopic compositional information from the object. Spectroscopic compositional information can be obtained from the spectrum of the emission, or using photoemission excitation spectra. Determining the spectroscopic compositional information does not preclude the determination of stereoscopic vision information and is a departure from conventional methods.

Stereoscopic vision information includes the direction of the surface normal at one point on the object surface from the monocular viewpoint, or a surface height profile of the object. In a preferred embodiment, the receiver is a camera. If the receiver is a camera, the entire surface height profile is optionally determined. The stereoscopic vision shape of the object is determined by the surface height profile.

Surface height profiles are calculated by mathematical techniques used in conventional polarimetry. Images are recorded at different times where the brightness of each pixel increases with the photoemission emission intensity of the corresponding object point. For example, a first image is recorded at a first polarization state of incident radiation, and a second image is recorded at a second polarization state of incident radiation.

Any conventional appropriate method is used to calculate three-dimensional information from monocular polarimetric photoemission images, including the methods described in J. R. A. Torreão and J. L. Fernandes, "Matching photometric stereo images", *J. Opt. Soc. Am.*, A15(12), 2966-2975, (1998) and J. R. A. Torreão, "Natural Photometric Stereo", *Anois do IX Sibgrabi*, 95-102 (October 1996). The calculation of three-dimensional information has not developed to the extent possible in the field, presumably as it is easy to overestimate the degree to which photoemission destroys polarimetric information of the illuminating source. However, the interaction between surface and incident radiation causes some polarimetric information to be preserved, even in the case of photoemission.

Polarimetric photoemission requires that the object reference surface must have both specular reflectance and some photoemission (such as fluorescence, phosphorescence, or Raman). The object reference may be a natural feature, or a man-made object. The object reference may be a natural or man-made object. For example, an object may be positioned a certain distance from the apparatus by placement, firing a projectile, dropping from an aircraft, or other method, at the time of measurement or at some earlier time. The object may include an electronic circuit or transponder, so as to facilitate determination of the object distance. In other examples, a locator device may be placed on a natural object. The object can be an object chosen to have desired properties, such as photoemission or diffuse scattering. The object can be remote from the apparatus.

The object reference optionally includes a material having known specular reflectivity. If an object has known specular reflectivity, the surface of the object does not have significant amounts of concavity or roughness. A shiny material has only specular reflectance, while a glossy material has only both specular and diffuse reflectance.

A wavelength selective device in front of the receiver can be used to block out the specular reflection from a glossy material. For example, a filter passing the photoemission wavelength while absorbing the excitation wavelength is optionally used.

Materials with both specular reflection and photoemission are common. An example would be plastic devices. The covering of plastic devices is generally smooth and flat, and plastic materials often have high fluorescence efficiencies, particularly if excited at UV wavelengths. Hence, the inventive method is operative for the detection and identification of plastic devices.

Figure 2:
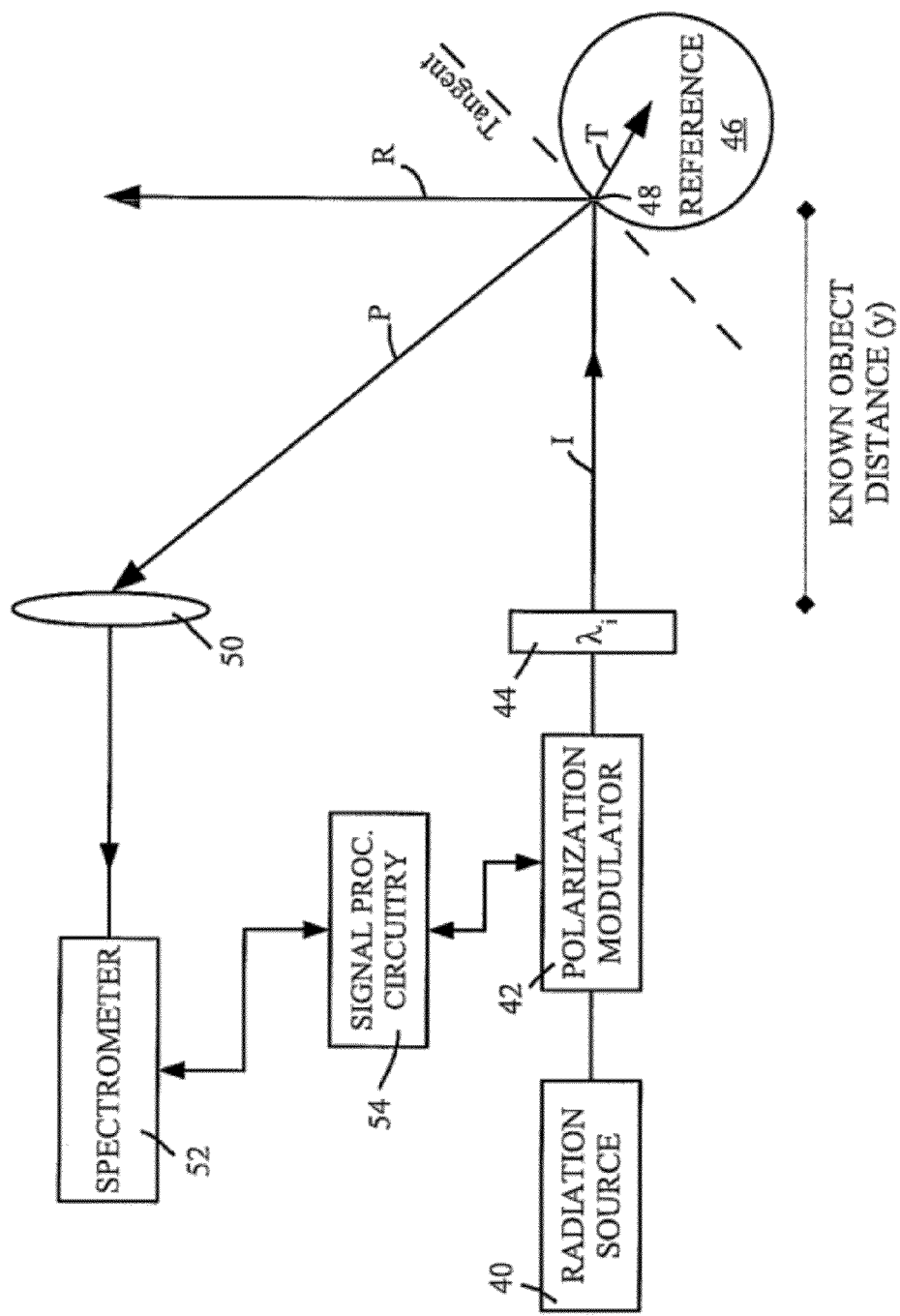
FIG. 2 shows a schematic of an alternative inventive apparatus for remote polarimetric photoemission imaging.

FIG. 2 shows how spectroscopic information is determined at the same time as stereoscopic vision information. FIG. 2 shows a schematic of an apparatus for remote polarimetric photoemission for both stereo imaging and spectroscopy; using one polarization modulator and a spatial camera-like receiver. I is the incident beam, R is the specular reflected beam, T is the transmitted beam, and P is the path of the emitted photoemission radiation. The apparatus comprises a radiation source 40, a polarization modulator 42, and excitation wavelength filter 44. The filter 44 is a narrow band filter at an excitation wavelength $\lambda_i$. The incident radiation is incident on the surface of an object reference 46, at point of incidence 48 after passing through a known object distance (y) between the object reference 46 and the filter 44. FIG. 2 shows a tangent to the surface at the point of incidence 48 as a dashed line. A specular reflection beam is produced, labeled R. A portion of the incident energy is transmitted into the object, as transmitted beam T, where it excites photoemission. The photoemission (P) is collected by lens 50, and is incident on spectrometer 52 synonymously described as a detector. The signal processing circuitry 54 allows correlation of the detected photoemission intensity with the incident polarization, and determination of both three-dimensional data and surface spectral properties of the object. The above-referenced numerals detailed with respect to FIG. 2 have the same meaning as provided for the same term in regard to FIG. 1.

In FIGS. 1 and 2, electromagnetic radiation from a radiation source 10 or 40 such as a laser passes through a polarization modulator 12 or 42, respectively, a device that changes polarization as a function of time. The source 10 or 40 emits electromagnetic radiation with a wavelength of incidence, designated $\lambda_i$. Electromagnetic radiation is transmitted through a medium, such as the atmosphere, water, or vacuum, until it reaches object reference 16 or 46. Electromagnetic radiation from the source is incident on the object at an incidence angle $\theta_i$. A part of the electromagnetic radiation is reflected, by specular reflectance, from the surface of the object at a reflection angle that is the same as the incidence angle, $\theta_i$. Part of the incident electromagnetic energy (I) is transmitted through the surface (T) of the object 16 or 46, and excites photoemission (P) at a wavelength, $\lambda_p$, where $\lambda_p > \lambda_i$. The specular reflectance varies with incident polarization, so the refracted transmittance varies with incident polarization, so the photoluminescent emission intensity (P) varies with incident polarization. Therefore, the emission intensity will also vary with time, because the incident polarization varies in time. The reflectance (R) also varies with angle of incidence. Because the radiation source is collimated or otherwise fixed in direction, the angle of incidence varies over the surface of the object, and so the depth of variation in emission intensity varies over the surface of the object reference.

In examples of the present invention, the degree of polarization of the polarimetric photoemission signal is determined, and used to determine three-dimensional data. The photoemission emission intensity is correlated with the polarization of the radiation that excites the photoemission.

Radiation Source (Synonymously Transmitter)

Figure 3:
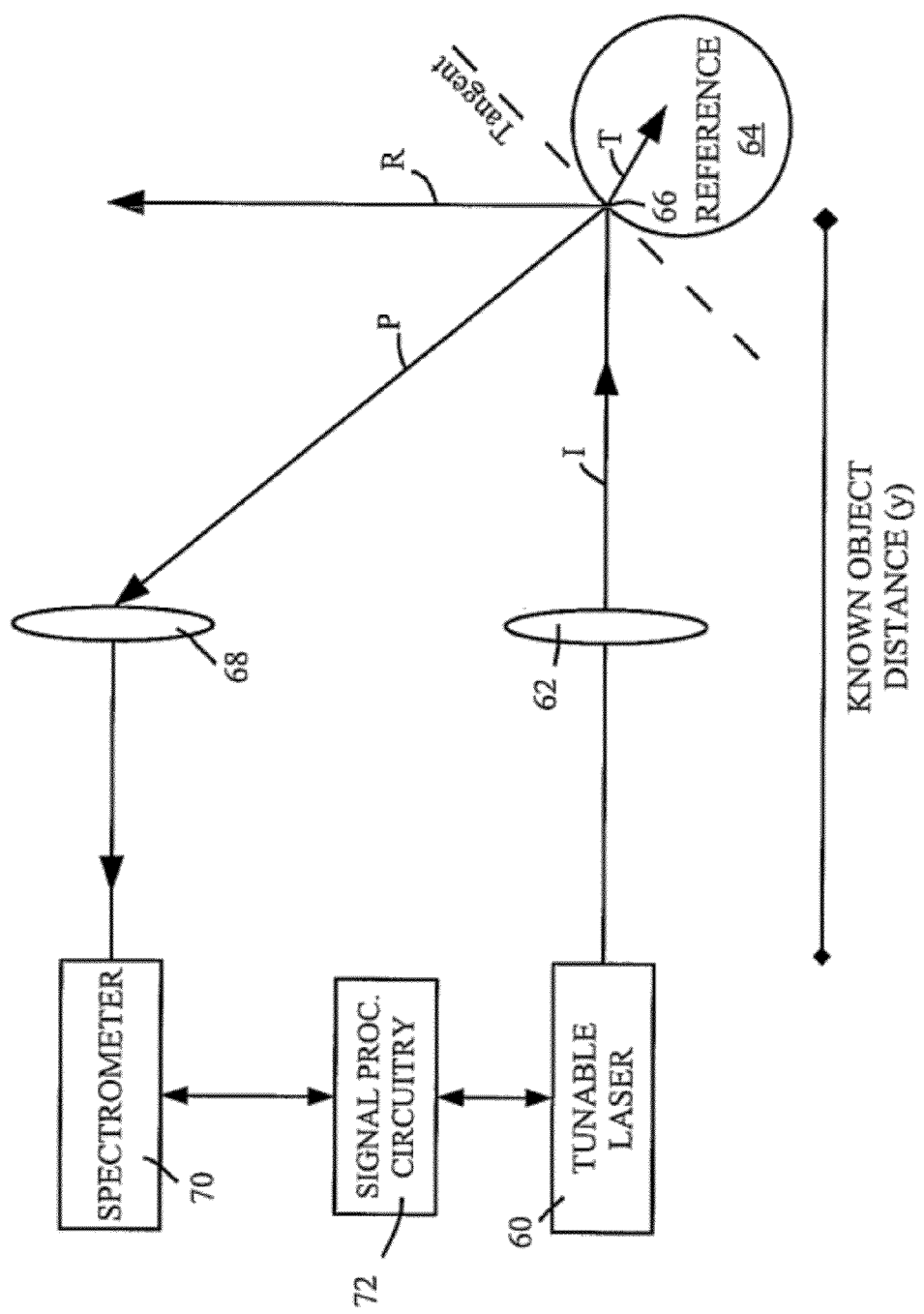
FIG. 3 shows a schematic of alternative apparatus for multiple polarimetric photoemission.

FIG. 3 shows a schematic of an inventive apparatus for a remote polarimetric photoemission and spectroscopy using a tunable pulse-modulated laser 60 operating in synchronicity with a spectrometer 70 with signal processing circuitry 72 providing data communication therebetween to allow for polarimetric photoemission processing to devolve stereo imaging and spectroscopy with a single beam and spectrometer. With a tunable laser 60 operating as the radiation source and positioned a known object distance (y) from the object preference 64, the polarization of the instant of the instant beam I is a characteristic of the instant beam I across a known object distance thereby obviating the need for a polarization modulator and a narrow band filter as detailed with respect to FIGS. 1 and 2. Rather, a lens or collection of lenses depicted generally at 62 in FIG. 3 are provided in concert with collection lens 68 intermediate between a point of incidence 66, the object reference 64, and a spectrometer 70. With respect to FIG. 3, spectrocomponents T, R, P and like meanings as ascribed the symbols used with respect to FIGS. 1 and 2. In instances where a known object distance, y is ascertained between a tunable laser 60 and object reference 64, monocular three-dimensional imaging the object reference 64 is obtained by a simplified optical path relative to FIGS. 1 and 2.

Figure 4:
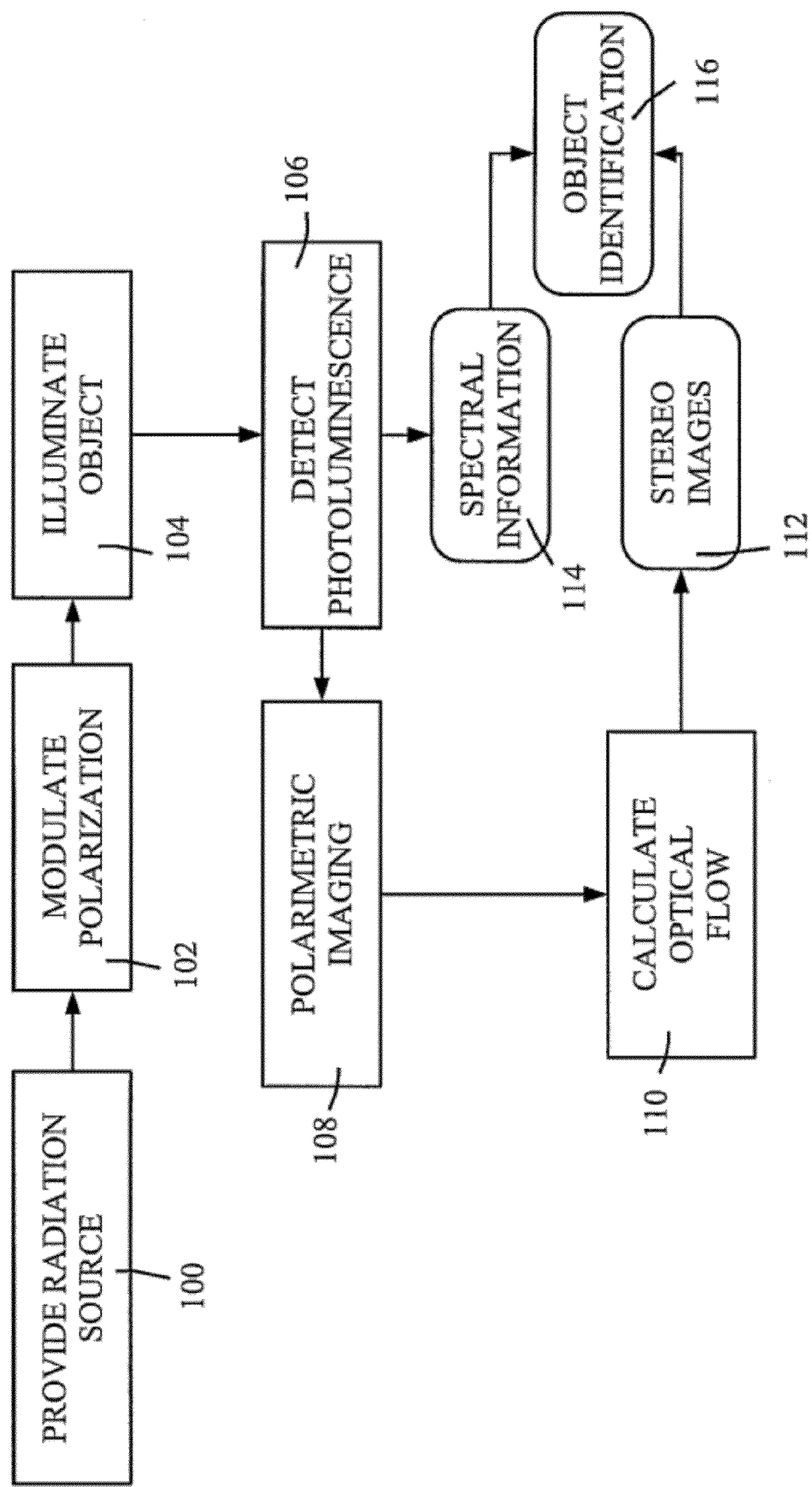
FIG. 4 is a process schematic and an inventive methodology for determining three-dimensional information relating to a remote object by monocular polarimetric imaging.
Figure 5:
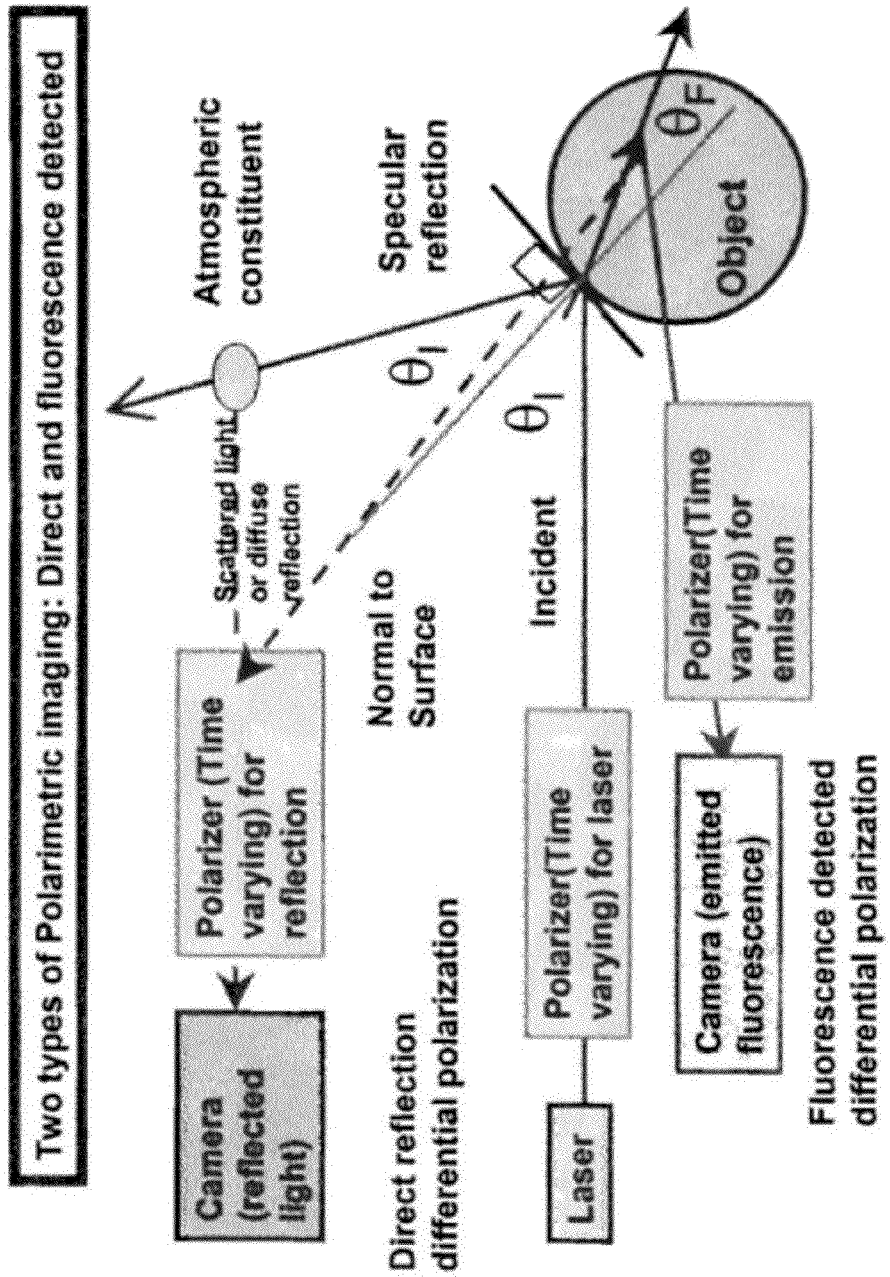
FIG. 5 is a schematic block diagram illustration of two types of polarimetric Imaging: Direct and Fluorescence Detection.

An inventive method schematic is provided with reference to FIG. 4 for the determination of three-dimensional information relating to an object without resort to binocular imaging, and instead using monocular polarimetric imaging. One provides a radiation source 100 with the output incident radiation impinging on the object reference having a time-dependent polarization inclusive of multiple initial polarization states. The time-dependent polarization being afforded by modulating polarization at step 102 is performed with reference to any of the aforementioned FIGS. 1-3 to illuminate an object 104. It is appreciated that an object distance is known relative to narrow band pass filter, per FIGS. 1 and 2, or a tunable laser transceiver, per FIG. 3. Through detection of photoluminescence 106 from the object detected photoluminescence intensity data associated with the object while it is used to create images of the object that vary in incident light polarity at step 108. Through polarimetric imaging 108, the same object is a function of light polarity, optical flow is calculated at step 110 to in effect overlap the polarimetric images and derive stereo images 112. Regarding the terminology "Optical flow," in the publication by B. K. P. Horn and B. G. Schunk, "Determining Optical Flow", MIT Artificial Intelligence Laboratory, 572, 0-27 (1980), hereby incorporated by reference, there is a description of a method for finding optical flow. Optical flow is defined in the article as:

Optical flow is the distribution of apparent velocities of movement of brightness patterns in an image. Optical flow can arise from relative motion of objects and the viewer [citation omitted]. Consequently, optical flow can give important information about the spatial arrangement of the objects viewed and the rate of change of this arrangement [citation omitted]. Discontinuities in the optical flow can help in segmenting images into regions that correspond to different objects.

According to the "Determining Optical Flow" article, in general optical flow cannot be computed locally, since only one independent measurement is available from the image sequence at a point, while the flow velocity has two components. A second constraint is needed. A method for finding the optical flow pattern is presented in the "Determining Optical Flow" article which assumes that the apparent velocity of the brightness pattern varies smoothly almost everywhere in the image. An iterative implementation is shown which successfully computes the optical flow for a number of synthetic image sequences. The algorithm used in "Determining Optical Flow" article reportedly can handle image sequences that are quantized rather coarsely in space and time and is, reportedly, insensitive to quantization of brightness levels and additive noise. Examples are included where the assumption of smoothness is violated at singular points or along lines in the image.

It is appreciated that photoemission intensity data used to calculate polarimetric imaging 108 from four or more initial polymerization states is optimal for determining three-dimensional information relating to the object reference illuminated at step 104. The photoluminescence detected at step 106 also provides spectral information providing information as to a composition of the object illuminated at step 104. The spectral information 114 is particularly useful in distinguishing an object from a decoy in the same three-dimensional contours provided of a different compositional material. Evaluation of the spectral information at step 114 is facilitated by comparing the spectral information at 114 against a spectral library of known compositions. In instances when both spectral information 114 and stereo images 112 are collected with respect to a given illuminated object 104, a remote object identification 116 is perfected that provides through monocular illumination information about the three-dimensional contour and composition of the object. As such, the present invention is particularly useful in the identification of remotely detected objects even when attempted to be camouflaged as well as discerning a decoy version of the object from the actual object itself.

Other Exemplary Apparatus

The transmitter and receiver are optionally disposed within a single housing, to form a unitary apparatus. The apparatus may be carried or otherwise supported by a land vehicle, boat, submarine, aircraft, satellite, a person, or may be set on the ground, for example using a stand.

The inventive apparatus optionally also includes a display, which may be used to provide a visual indication of determined data. The display also is useful to show the part of the environment towards which the incident radiation is directed, for example in combination with zoom or image enhancement capabilities, in order to direct the incident radiation onto the surface of the desired object. A camera optionally is used to image the reference object, the same camera being used as a sensor in the receiver, and/or for photometric stereo measurements.

In other inventive embodiments, the transmitter and receiver are contained in separate housings, and are in data communication through a cable or wireless communications link. It is appreciated that multiple transmitters and/or receivers optionally are used, for example to allow data to be collected for multiple angular positions, wavelengths, object distances, and the like.

An inventive apparatus optionally provides for collection of other ambient condition data, such as temperature, pressure, humidity, other meteorological conditions such as cloud cover, precipitation, time, sun position, pollutant analysis, particulate form and concentration, altitude, position (for example, using a GPS), and the like. Atmospheric depolarization may be correlated with ambient conditions, and may be used to interpret data collected under similar conditions.

An apparatus also optionally includes an operational mode selector, the operational mode selector having a first setting in which photoemission is detected, and a second setting in which diffuse reflection is detected.

An apparatus also optionally includes a data input, which can be the data input of the computer, the data input receiving the object distance so as to allow determination of the depolarization efficiency.

Ambient condition data is collected by instrumentation included within the device, received directly from other devices over a communications link, or may be entered by an apparatus operator using a data entry mechanism.

The apparatus also optionally includes a housing, which in some examples may seal against ingress of the medium under test (for example, if the medium is water, such as seawater). The housing may be provided with one or more windows to allow radiation to enter and/or leave the housing.

Other Examples

It is appreciated that an inventive apparatus optionally includes additional functionality. For example, the apparatus may additionally be used to measure photoemission spectra, such as fluorescence spectra; simultaneous polarimetric fluorescence and photometric stereo imaging. In polarimetric fluorescence imaging, both geometric and chemical information are determined for the surface of an object surface, even where the object surface has unknown surface or compositional properties.

For example, an inventive apparatus readily determines atmospheric depolarization using an object, as described in copending application Ser. No. 12/940,228, filed Nov. 5, 2010 entitled "SYSTEM AND METHOD FOR MEASURING DEPOLARIZATION." The atmospheric depolarization is then used in improved photometric stereo measurements by methods and apparatus illustratively including those detailed herein for the present invention.

Optical Flow Theory for Atmospheric Calculations

The mathematics for finding the optical flow are presented in the following. Optical flow can give important information about the spatial arrangement of objects viewed and the rates that characterize change of this arrangement for objects in the atmosphere. A 3-dimensional image can be extracted from a single view through the atmosphere, using a sequence of 2-dimensional images, to calculate optical flow. Optical flow is the apparent velocity of a localized region on the image, which can be calculated from two images of different wavelength. Optical flow at a coordinate, and an image at a particular wavelength, $\xi$, are defined by a pair of equations for the two components, which are $$D_x(x, y, \xi) = \frac{dx}{d\xi},$$

and $$D_y(x, y, \xi) = \frac{dy}{d\xi},$$

where Dx is the x-component of optical flow, Dy is the y-component of the optical flow, $\xi$ is the wavelength of the image, and the spatial coordinates of the brightness element on the object are designated by the coordinates x and y. The expression "brightness element" is used here in analogy to "fluid element," because the mathematics of optical flow is analogous to fluid flow where the wavelength, $\xi$, in optical flow is analogous to time, t, in fluid flow.

The optical flow at each image point x and y can be calculated using two consecutive images that can be described as brightness value matrices. The brightness element is defined so that its brightness is constant in wavelength. The rate that brightness changes with respect to wavelength is zero, which means $$\frac{dE(\vec{s})}{d\xi} = 0.$$

where E is the brightness of the element at point $\vec{s} = x\hat{n}_x + y\hat{n}_y$, and the wavelength is $\xi$.

The chain rule of differentiation applies to the rate of changing brightness. A continuity condition can be derived from the chain rule by $$\frac{\partial E}{\partial x}\frac{dx}{d\xi} + \frac{\partial E}{\partial y}\frac{dy}{d\xi} + \frac{\partial E}{\partial \xi} = 0,$$

where the partial derivatives of the brightness are $$E_x = \frac{\partial E}{\partial x},$$

$$E_y = \frac{\partial E}{\partial y},$$

and $$E_\xi = \frac{\partial E}{\partial \xi}.$$

The condition of continuity is a constraint necessary to specify a unique solution to the surface depth. However, condition of continuity is insufficient to calculate a unique solution to the optical flow. The perceived direction of optical flow will always be in the direction parallel to the gradient of brightness. If the optical flow component that is parallel to the brightness gradient in the xy-plane is designated as $D_{xy}$, where $$\vec{D}_{xy} = D_x\hat{n}_x + D_y\hat{n}_y,$$

then the continuity condition can be shown to be equivalent to $$\vec{D}_{xy} = -\frac{E_\xi}{\sqrt{E_x^2 + E_y^2}}\hat{n}_{xy}$$

where $\hat{n}_{xy}$ is a normalized vector parallel to the gradient of brightness on the image (i.e., xy) plane.

In the photometric stereo method, two images are used to calculate the surface depth value, designated as z, of a perceived 3D object. The slopes of the surface depth on the perceived object is then defined by p and q where:

$$p = -\frac{\partial z}{\partial x}$$

and $$q = -\frac{\partial z}{\partial y}.$$

The components p and q are proportional to $|D_x\hat{n} + D_y\hat{n}|$ which is the magnitude of the optical flow. The component of optical flow, D (arrow), that is perpendicular to the brightness gradient, E (arrow), cannot be determined without another constraint. Constraints are necessary to determine a unique optical flow, which is necessary to calculate a unique surface depth function. Both analytical and numerical algorithms are available for calculating the optical flow.

Methods of calculating optical flow were developed by Horn and Schunk, which are shown in Horn & Schunk, "Determining Optical Flow," MIT Artificial Intelligence Laboratory Memo, 572, 0-27 (1980). The constraint that was used in this study was the smoothness constraint, which limits the motion of the image in a way that the image can be visualized as sliding on the surface of the object being imaged.

The equations for optical flow can be solved using numerical method as described. To digitize E, Dx and Dy, integer values are assigned to x, y, and ξ so $$x \to j,$$

$$y \to i,$$

$$\xi \to k$$

where i, j, k=0, . . . , $N_{x,y,z}$. The local partial derivatives of $\overline{E}$ are averaged for a cube of adjacent values of i, j, and k by $$\overline{E}_x = \frac{1}{4}\{(E_{i,j+1,k} - E_{ijk}) + (E_{i+1,j+1,k} - E_{i+1,j,k}) +$$

$$(E_{i,j+1,k+1} - E_{i,j,k+1}) + (E_{i+1,j+1,k+1} - E_{i+1,j,k+1})\}$$

$$\overline{E}_y = \frac{1}{4}\{(E_{i+1,j,k} - E_{ijk}) + (E_{i+1,j+1,k} - E_{i,j+1,k}) +$$

$$(E_{i+1,j,k+1} - E_{i,j,k+1}) + (E_{i+1,j+1,k+1} - E_{i,j+1,k+1})\}$$

$$\overline{E}_\xi = \frac{1}{4}\{(E_{i,j,k+1} - E_{ijk}) + (E_{i+1,j,k+1} - E_{i+1,j,k}) +$$

$$(E_{i,j+1,k+1} - E_{i,j+1,k}) + (E_{i+1,j+1,k+1} - E_{i+1,j+1,k})\}$$

where $\overline{E}_x$, $\overline{E}_y$, and $\overline{E}_\xi$ are the average values of $E_x$, $E_y$, and $E_\xi$, at a point designated by i, j, and k.

The optical flow, $D_x$ and $D_y$, is calculated from the averaged derivatives by an iterative algorithm that was published by Horn and Schunk, "Determining Optical Flow," MIT Artificial Intelligence Laboratory Memo, 572, 0-27 (1980). The $D_x$ and $D_y$ are reassigned as u and v to match the nomenclature of that article. If $u^{(n)}$ and $v^{(n)}$ represents the calculated value for u and v at a point designated by integers I, j and k, where n designates a step of the iteration, then the (n+1) step is $$u^{(n+1)} = \overline{u}^{(n)} - \overline{E}_x[\overline{E}_x \overline{u}^{(n)} + \overline{E}_y \overline{v}^{(n)} + \overline{E}_\xi]/[\delta^2 + \overline{E}_x^2 + \overline{E}_y^2]$$

$$v^{(n+1)} = \overline{v}^{(n)} - \overline{E}_y[\overline{E}_x \overline{u}^{(n)} + \overline{E}_y \overline{v}^{(n)} + \overline{E}_\xi]/[\delta^2 + \overline{E}_x^2 + \overline{E}_y^2]$$

where $\overline{u}^{(n)}$ and $\overline{v}^{(n)}$ are the averaged values of the optical flow components at iteration n and $\delta^2$ is an input parameter less than or equal to $\overline{E}_x^2 + \overline{E}_y^2$. The numerical parameter, $\delta^2$; partially compensates for computational noise in $\overline{E}_x$, $\overline{E}_y$, and $\overline{E}_\xi$. The input parameter, $\delta^2$, has a small value ($0 \leq \delta^2 \leq \overline{E}_x^2 + \overline{E}_y^2$) that should be set at greatest accuracy to the anticipated noise value of $\overline{E}_x^2 + \overline{E}_y^2$. However, the iterative algorithm will converge eventually even for $\delta^2 = 0$.

The value of $u^{(n+1)}$ and $v^{(n+1)}$ do not directly depend on $u^{(n+1)}$ and $v^{(n+1)}$, but does depend on their averaged local values $\overline{u}^{(n)}$ and $\overline{v}^{(n)}$ calculated by the following weighted averaging formulas:

$$\overline{u}_{ijk}^{(n)} = \frac{1}{6}\{u_{i-1,j,k}^{(n)} + u_{i,j+1,k}^{(n)} + u_{i+1,j,k}^{(n)} + u_{i+1,j,k}^{(n)}\} +$$

$$\frac{1}{12}\{u_{i-1,j-1,k}^{(n)} + u_{i-1,j+1,k}^{(n)} + u_{i+1,j+1,k}^{(n)} + u_{i+1,j-1,k}^{(n)}\}$$

$$\overline{v}_{ijk}^{(n)} = \frac{1}{6}\{v_{i-1,j,k}^{(n)} + v_{i,j+1,k}^{(n)} + v_{i+1,j,k}^{(n)} + v_{i+1,j,k}^{(n)}\} +$$

$$\frac{1}{12}\{v_{i-1,j-1,k}^{(n)} + v_{i-1,j+1,k}^{(n)} + v_{i+1,j+1,k}^{(n)} + v_{i+1,j-1,k}^{(n)}\}$$

If $E_{ijk}$ is, for each k, an $N^{i+1}+1$ by $N_{j+1}+1$ matrix (i.e., i=0, 1, 2, 3, . . . , $N_i$ and j=0, 1, 2, 3, . . . , $N_j$), then the optical flow at each k is an $N_i$ by $N_j$ matrix.

The initial values (n=0) of the optical flow components can be chosen as zero, $$\overline{u}_{ijk}^{(0)} = \overline{v}_{ijk}^{(0)} = 0$$

although a better initial value may facilitate convergence. The constants ⅙ and 1/12 were chosen to optimize convergence using a cube of local values determined by the two images at different wavelengths designated by integers k and k+1.

Fluorescence Imaging and Signatures by Time Varying Differential Polarization of Laser-Light Through the Atmosphere A preferred embodiment is directed towards detection of both concealed targets and personnel through a variety of airborne and ground based sensor efforts to enable detection of both camuouflaged targets and personnel in camouflaged or atmospherically obscured environments. The method, remote polarimetric fluorescence, utilizes laser light with time-varying differential polarization to excite a material that emits fluorescence with time-varying intensity) which can be used for imaging the target. The intensity of emission varies because the fluorescence emission is anticorrelated with specular reflectance that itself varies strongly with polarization. Signatures useful for detecting personnel include substances that are strongly fluorescent (e.g., oil, dyes)) and surface configurations characteristic of personnel, such as facial features and body profiles. The coupling between fluorescence and specular reflectance results in an image that will be more chemically specific than images acquired by non-fluorescent methods, and less sensitive to atmospheric obscuration than fluorescence imaging excited by a, source with constant polarization. Calculations using published experimental data for depolarization were for a military related scenario were performed. The calculated values are shown to suggest how much error depolarization will cause in remote polarimetric fluorescence imaging.

There exists a problem of detecting personnel in camouflaged or atmospherically obscured environments, which may be addressed through a variety of airborne and ground based sensor efforts. These efforts include electromagnetic radiation (EMR) at a variety of wavelengths, ranging from millimeter to optical wavelengths. Many methods are needed because the concealed target threat comes from a variety of conditions.

An optical-wavelength method of remote polarimetric fluorescence imaging may be useful for detecting personnel in camouflaged or atmospherically obscured environments. In this method, time-varying differential polarization in laser light transmitted through the atmosphere excites fluorescence emission from an illuminated object. The fluorescence emission intensity is anticorrelated with specular reflectivity because specularly reflected light does not excite fluorescence (i.e., specularly reflected light can't be absorbed by the material). The fluorescing object is detected as images separated by time intervals that vary in emission intensity. The differences between fluorescent image intensities at different time intervals show features that are enhanced by the increase in specular reflectance at oblique incident angles. Many substances strongly fluoresce (e.g. ~oil on skin, dyes} plastic) and features on the objects surface (faces, flatness) are signatures that signify personnel or equipment. Materials that could be a background, such as vegetation, do not fluoresce as strongly as the signature materials. The coupling between fluorescence and specular reflectance results in an image that will be more chemically specific than images acquired by nonpolarization methods, and less sensitive to atmospheric obscuration than fluorescence imaging excited by a source with constant polarization. Therefore, differential polarized reflectance detected using fluorescence may be useful for distinguishing personnel and camouflaged targets. Imaging through the atmosphere is difficult due to the absorption and scattering of light by atmospheric particles that include molecules, water droplets, and aerosols. The image produced from reflected light often cannot be distinguished from light scattered from atmospheric constituents. Efforts to remedy this problem have used various optical properties. The combination of fluorescence, specular reflection, and differential polarization may be useful for distinguishing personnel and camouflaged targets. The differential specular reflectance of the target surface is correlated with the polarization of the incident EMR. If the angle of incidence of light on a surface is nonzero, greater than 0°, and less than the critical angle, $\theta_c$, there is a higher reflectance for one polarization state (e.g., s-polarization) than the polarization orthogonal to it p-polarization). EMR with an electric field perpendicular to the normal of the surface of the target is s-polarized, while EMR with the magnetic field perpendicular to the normal to the surface of the target is p-polarized. The differential polarization reflectance is nonzero for all $\theta_I$ satisfying $0<\theta_I<\theta_c$ where $\theta_c$ is the critical angle.

The remote polarimetric fluorescence method may not obscured by atmospheric particles under some atmospheric conditions. Laser EMR that reaches the target material in just a few forward scattering events is not as randomized as laser EMR that is either scattered many times before it reaches the target material or scattered at a significant nonzero angle. Therefore, images produced by polarization differential polarization reflectance will be less vulnerable to atmospheric scattering background than images generated from polarization-average (i.e., unpolarized) reflectance. Furthermore, the longer the wavelength the weaker the scattering from small particles. Therefore, the fluorescence emission would propagate through the atmosphere from the material object with less scattering than the laser-excitation because the peak emission wavelength is longer by Stokes Law.

The use of differential polarized reflectance for imaging has a limitation that may have prevented differential polarization reflectance from working effectively. The EMR transmitted to the target is depolarized by the atmospheric particles. The impact of atmospheric depolarization on remote fluorescence polarimetry may be analyzed. Fluorescence-detected differential-reflectance by polarized excitation is presented as a possible process with chemical specificity that can be used to make better images by polarization imaging.

Theory of Remote Polarimetric Fluorescence Imaging

Regarding the theory of the remote sensing technique, first described are techniques of in-situ fluorescence-detected polarization dichroism. Then, the remote imaging method based on fluorescence-detected polarization dichroism may be described in terms of the previously described in-situ techniques.

In-Situ Fluorescence-Detected Differential Polarization of Incident Radiation for Materials Embedded in Atmosphere Differential polarization of the electromagnetic radiation (EMR) impinging on an insitu fluorescent target can be detected and degree of polarization determined by measuring the intensity of fluorescence emitted from the target embedded in the atmosphere. Fluorescence is a process where EMR is incident on a material at an excitation wavelength, some energy from the incident EMR is absorbed, and then part of the energy is emitted at an emission wavelength. Because the emission energy is proportional to the energy absorbed from the incident EMR, but with a different wavelength, background can be subtracted using optical filters. Several in-situ techniques for chemical analysis and analytical microscopy have been previously developed and used.

For example, fluorescence-Detected Polarization-Dichroism (FDPD) is a technique that has become extremely useful for studying molecules. FDPD consists of time-varying the polarization of an excitation EMR wave, and measuring the changes in fluorescence intensity associated with the changing polarization. Fluorescence-detected circular dichroism (FDCD) and fluorescence-detected linear dichroism (FDLD) are both variations on FDPD. Although polarization dichroism can be detected by transmission instead of by fluorescence, changes in transmission are small compared to the transmission. The signal is a small fluctuation in transmission that has to be detected over a large background and can be very noisy. The emission (fluorescence) wavelength is longer than the excitation (incident) wavelength~which makes separation easier than in the case of absorption. FDCD is useful for studying chiral molecules that comprise optically active materials. The differences in fluorescence intensity for incident EMR polarized in two orthogonal, circularly polarized states are measured in FDCD. Circular dichroism is a property of asymmetric molecules. FDCD spectra are often easier to obtain than absorption-detected circular dichroism spectra because fluorescence can be separated from the transmitted EMR using an optical filter. However, uncontrolled birefringences in the environment severely bias FDCD. FDLD is useful for studying the orientation of molecules. The differences in fluorescence intensity for incident EMR polarized in two orthogonal, linearly polarized states. Linear dichroism is a property of molecules that are lined up in the same direction. Studies have used FDLD to determine the orientation of molecules on surfaces. FDLD has been used for microscopy and in situ chemistry, but not for remote sensing. FDLD signals are usually much stronger than FDCD signals; so that FDCD are less biased by uncontrolled birefringences than FDLD. The method investigated in this study is based on FDLD. Although the efficiency of fluorescence is much less than that of reflection, optical filters that block at the excitation rather than the emission wavelength can reduce background including both randomly scattered laser EMR and randomly scattered emission.

Both methods, FDCD and FDLD, have demonstrated that differential absorption in polarization can be measured in-situ with a differential intensity in emission. The insitu success of these methods suggests that they may also be used effectively in remote polarimetric fluorescence imaging.

Depolarization Rate of Electromagnetic Radiation Caused by Atmospheric Particles The rate of depolarization of electromagnetic radiation (EMR) in the atmosphere greatly impacts remote polarimetric fluorescence and other polarmetric techniques. An equation for depolarization that is useful in evaluating the depolarization on polarimetric systems is derived here for the purpose of remote polarimetric fluorescence.

A beam of electromagnetic radiation (EMR) with nonzero differential polarization propagating in the atmosphere in a fixed direction (i.e., scattering angle at θ=0°) undergoes both scattering and absorption by atmospheric particles. EMR energy is lost from the beam by both absorption, which removes EMR energy, off-axis (i.e., scattering angle approximately 0°) and backscattering (i.e., scattering angle θ=180°), which redirect the EMR energy out of the beam. However, forward scattering (i.e., scattering angle approximately 0°) does not either remove or redirect the energy, so that the EMR energy is still part of the beam. The forward scattering process changes the polarization state of the beam in a decrease of differential polarization. In a disordered medium such as the energy that is scattered becomes randomly polarized (i.e., unpolarized). The energy that isn't absorbed or scattered preserves its polarization state. In the case of EMR that initially is fully polarized, the total intensity of EMR that has not changed either its direction of propagation nor its polarization state is proportional to the difference (E) in intensity between s-polarized and p-polarized components. EMR with an electric field vector perpendicular to the normal of a surface that it is incident upon the surface is s-polarized, while EMR with a magnetic field vector perpendicular to the normal of the surface is p-polarized. The difference, E, between the intensity of components that are s or p polarized, decreases with distance both because of loss of energy to the beam, which is designated as extinction, and by forward scattering processes that randomize the polarization state, which is designated depolarization. The beam of EMR that excites a point on the target can be characterized either by an irradiance (unit $Wm^{-2}$) value for a cross sectional area on the beam, E, or by a radiance (unit $Wm^{-2}sr^{-1}$) function of angle from every point on the same cross radiance of the beam) $L(\theta, \Phi)$. The relationship of radiance and irradiance is described by a integration over solid angle as defined by the photometric relationship equation $$E = \int_{4\pi} L(\theta, \Phi) d\Omega$$

where $d\Omega = \cos\theta d\theta d\Phi$

If the EMR is collimated in the forward direction, the radiance that fulfills the photometric relationship relation is proportional to a delta function in solid angle. For the energy of the part of the beam that has neither been lost to extinction or forward scattered, the equation for L is $$L(\theta, \Phi) = E\delta(\cos\theta, \Phi)$$

where E is the irradiance of the beam. The delta function, δ, is defined by $$1 = \int_{\Omega} \delta(\Omega') d\Omega'$$

for a solid angle region Ω that includes θ=0° and $$0 = \delta(\Omega')$$

for a solid angle region Ω that doesn't include θ=0°.

The radiative transfer equation is applicable if there is more single particle scattering is much larger than multiparticle scattering. The predominance of single particle scattering applies to E because of the assumption that any scattering event depolarizes the EMR (i.e., the differential polarization is lost from the very first scattering event in a multiscatter event). Then, the attenuation of the beam can be derived using the radiative transfer equation in the following form $$\frac{dL}{ds} = S - \beta L + \frac{\sigma}{4\pi} \int L(\vec{r}) \Phi(\vec{r}, \vec{s}) d\Omega_r$$

where s(arrow) is the path vector, r(arrow) is the position of scattering on the cross section, β is the extinction coefficient, σ is the scattering coefficient for forward scattering that changes the polarization, Φ is the quantum efficiency for scattering from r(arrow) to s(arrow), and S is the source term for points on the path, $d\Omega_r$ represents the infinitesimal solid angle subtended by a target point that collects energy from the beam. The beam is propagating in the z direction, θ is the polar angle and Φ is the azimuthal angle (i.e. S is negligible for the examples discussed in these examples (i.e., S=0).

Depolarization comes from contributions of the scattering of separate infinitesimal solid angles). So the total decrease in intensity is proportional to an integration of radiance over solid angle $\Omega_s$, resulting in $$\frac{d}{ds}\left[\int_{4\pi} L(r) d\Omega_s\right] = -\beta \left(\int_{4\pi} L(r) d\Omega_s\right) + \frac{\sigma}{4\pi} \int \left(\int_{4\pi} L(r) d\Omega_s\right) \Phi(\vec{r}, \vec{s}) d\Omega_r,$$

which when substituted in the equations for radiance of the beam results in the equation for depolarization $$\frac{dE}{ds} = -\beta E + \frac{\sigma}{4\pi} \int E\delta(\cos\theta_r, \phi_r) \Phi(\vec{r}, \vec{s}) d\Omega_r$$

where $\theta_r$ and $\phi_r$ are the angles of scattering for each point on the beam cross section.

Substitution of the definition of δ into the equation for polarization results in $$\frac{dE}{ds} = -\beta E + \frac{\sigma}{4\pi} \int E\delta(\cos\theta_r, \phi_r) \Phi(\vec{r}, \vec{s}) d\Omega_r$$

where $\Phi(\theta=0)$ is the quantum efficiency of the forward scattering process that changes polarization. The solution to this differential equation is well known, and can be expressed as $$E(s) = E_0 \exp\left(-\left[\beta + \frac{\sigma}{4\pi} E\Phi(\theta=0)\right]s\right)$$

where E(s) is the irradiance of depolarized EMR at point s, and $E_0$ is the irradiance of the depolarized EMR at s=0. However, the total intensity of EMR in the beam including both polarization components (i.e., when σ=0) is I where $$I(s) = I_0 \exp(-\beta s)$$

The degree of linear polarization in for the x and y axes is defined as $$P(s) = \frac{E(s)}{I(s)},$$

which after substitution of E and I into the definition of degree of polarization results in $$P(s) = P_0 \exp\left(-\left[\frac{\sigma}{4\pi} E\Phi(\theta=0)\right]s\right)$$

where $$P_0 = \frac{E_0}{I_0}.$$

The value of the constant $$\left[\frac{\sigma}{4\pi}E\Phi(\theta=0)\right]$$

is the rate of depolarization of a beam by atmospheric scattering. The equation for exponential decay of the degree of polarization can be rewritten as $$P(s) = P_0 \exp(-2_{qs})$$

where $$q = \frac{1}{2}\left[\frac{\sigma}{4\pi}E\Phi(\theta=0°)\right]$$

and $\Phi$ is the quantum efficiency of forward scattering that changes the polarization. The constant, q, is designated the depolarization efficiency. The limiting range due to depolarization can be calculated from q, once q is known. The distance over which total intensity can be measured is $x_I$, and the differential polarization can be detected is proportional to $x_P$. The distance, $x_P$, for the degree of polarization, P, to decrease by a factor of $e^{-1}$ is $$x_P = \frac{1}{2}q^{-1}.$$

The exponential decay of the degree of polarization has been shown to be valid where single-scatter events predominate over multiscatter or where the single-scattering event totally randomizes the polarization of EMR. This exponential relationship is useful for analyzing polarimetric devices.

Incident Polization State Affects Emitted Intensity of Fluorescence of Targets Embedded in the Atmosphere The equation for emitted EMR intensity as a function of polarization of the excitation beam (i.e., incident beam) is derived for a target, embedded in the atmosphere, consisting of a thin layer of paint or dye that fluoresces more strongly than the other materials around it. The equation for emitted fluorescence is $$L_{em} = h\Phi I_0 f(\lambda_{em}) K^i \gamma (\cos\theta)^{-1} M_i(\theta)$$

where $I_0$ is the intensity of excitation incident on the sample, $\Phi$ is the quantum efficiency of the thin layer material, h is the layer thickness, $f(\lambda_{em})$ is the normalized emission spectrum, $\theta$ is the polar angle where the excitation beam is propagating in the z direction, $\gamma$ is the product of concentration of fluorescent material and the molar absorption coefficient of the material at the excitation wavelength, $\lambda_{em}$ is the wavelength of emission, M represents the effects of reflection and scattering of emitted EMR at the surface of the material, and $T_i$ is the total effect of the direction of the excitation EMR angle, optical filter, excitation EMR scattering for the polarization state of incident EMR designated by i.

The intensity $I_{em}$ measured at a pixel that subtends a solid angle $\Omega$ is given by the irradiance formula $$I_{em} = \int_\Omega L(\Omega')d\Omega'$$

Substituting $L_{em}$ into $I_{em}$ results in $$I_{em} = h\Phi I_0 f(\lambda_{em}) T_i \gamma \overline{M}_i \Omega$$

where $$\overline{M} = \frac{1}{4\pi}\int M(\theta', \phi')d\Omega'$$

is the average transmissivity of the surface. If a parameter k is defined as:

$$k = h\Phi f(\lambda_{em})\gamma\overline{M}$$

then $$I_{em}^i = kI_0 T_i$$

where i is the polarization state at the excitation wavelength.

The parameter, $T_i$ is the transmittance for the incident laser beam of the surface from atmosphere to target material. For a smooth dielectric surface, $T_i$ can be calculated using the Fresnel equations. Although fluorescence emission has mostly random polarization, the intensity of the emitted EMR $I^i_{em}$ depends on the polarization of the excitation beam, designated by i.

Specular Reflectivity and Transmittance of Polarized EMR at the Electromagnetic Radiation, Atmosphere, and Target Material Interface Specular reflectance and transmittance of polarized EMR at the electromagnetic radiation (EMR), atmosphere, and target material interface is dependent on polarization. If electromagnetic radiation (EMR) is incident on a dielectric surface at an angle of incidence, $\theta_I$, part of the EMR undergoes specular reflection and part undergoes transmission from the surface. The incident, specularly reflected, and transmitted rays of EMR are shown in FIG. 1 as solid rays. The reflected EMR satisfies the specular law of reflection, which is the angle of incidence, $\theta_I$, is equal to the angle of reflection, $\theta_F$. The transmitted beam obeys Snell's Law, which is:

$$n_I \sin\theta_I = n_F \sin\theta_F$$

where $n_I$ is the index of refraction of the medium containing both incident and reflected rays, and $n_F$ is the index of refraction inside the object. In this discussion, the index of refraction of the atmosphere, $n_I = 1$, while the index of refraction of the target, $n_F > 1$.

Fresnel equations that describe the specular reflectances are:

$$R_s = \left(\frac{+\cos\theta_I - n_F\cos\theta_F}{+\cos\theta_I + n_F\cos\theta_F}\right)^2,$$

$$R_p = \left(\frac{-n_F\cos\theta_I - \cos\theta_F}{+n_F\cos\theta_I + \cos\theta_F}\right)^2.$$

Quantities may be calculated to compare $R_s$ to $R_p$. The polarization-averaged reflectance (R), differential polarization reflectance ($\Delta$), and the degree of linear polarization of reflectance (P) are expressed by $$R = \frac{R_s + R_p}{2},$$

$$\Delta R = R_s - R_p,$$

and $$P = \frac{\Delta R}{R}.$$

The EMR transmission for p-polarized EMR ($T_s$) s-polarized EMR ($T_p$), and the average polarization of EMR (T) are expressed by $$T_s = 1 - R_s,$$

$$T_p = 1 - R_p,$$

and $$T = 1 - R.$$

The emission intensity, $I_{Em}$ is proportional to the intensity of laser EMR in the material, which is proportional to the excitation intensity $I_o$, resulting in the following equation:

$$I_{Em} = k I_o T$$

where k is a constant. The proportionality to T is caused by reflection at the surface, because energy that doesn't transmit through the surface can't excite fluorescence under the surface. Analysis shows that, for $n_F > n_I$, if the incident EMR is transmitted into the target by the atmosphere at a nonzero angle, then $T_s < T_P$. Substitution shows that the signal $\Delta I_{Em}$ which is defined as $\Delta I_{Em} = k I_o (T_s - T_P)$ is positive. $\Delta I_{Em}$ is proportional to the signal in remote polarimetric fluorescence. Calculations were done to determine the polarization effect for $n_F = 1.5$ and $n_I = 1$.

Atmospheric Depolarization Equations

The depolarization of electromagnetic radiation (EMR) by transmittance through the atmosphere can be modeled by equations. The depolarization by the atmosphere can limit the range of remote polarimetric fluorescence imaging. Atmospheric particles scatter electromagnetic radiation (EMR) in a beam, with some EMR scattered in the direction of the beam. The depolarization by the atmosphere varies with atmospheric conditions and the path of the beam that is incident on the target. The shape and size of the atmospheric particles are part of atmospheric conditions. In particular, particles with spheroidal symmetry don't depolarize as efficiently as nonspherical particles. Lidar backscatter techniques are sometimes used to analyze the sphericity of atmospheric aerosol particles. However, Nonspherical particles are more likely to interfere with differential polarization imaging than spherical particles because spherical particles don't depolarize EMR propagating in the forward or backward directions. Water droplets (because of surface tension) and gas molecules (because they are smaller than a wavelength) are spherically symmetric. Therefore, backscatter-polarization lidar is a direct way of distinguishing spherically symmetric from spherically asymmetric particles. Nonspherical particles include dust and ice particles, which greatly depolarize radiation even in the forward and backward directions. A calculation of average depolarization efficiency from data published in an experimental study was done to show the usefulness of the depolarization efficiency. The experimental study has compared depolarization spherical and nonspherical particles using backscatter lidar at wavelength 532 nm. A depolarization coefficient that was characteristic of the atmosphere, averaged over a range, was not calculated. The calculation of depolarization efficiency is shown for the case where the depolarization process of the atmosphere is distributed continuously on the beam path going to and from the back scattering of the atmosphere. This is equivalent to the condition that all the depolarization is caused by multiple scattering in the forward direction of the beam, and the depolarization caused by a single backscattering event is negligible. The tendency of experimentally measured depolarization to increase with distance, x, rather than be constant over the entire range is consistent with continuously varying depolarization.

Backscattering lidar can be used to calculate the depolarization efficiency, q, which may be useful in evaluating the potential of fluorescence lidar imaging. A description of the mathematical method for calculating the depolarization efficiency from backscattering lidar data is presented.

The energy of EMR that is equally partitioned between horizontal and vertical polarizations on the target is U, and the total energy of the beam on the target is I. Then the signal is proportional to the degree of differential polarization of the excitation beam on the target, P, which is defined by:

$$P = U/T$$

The degree of polarization of EMR, approximately decays exponentially. The depolarization coefficient averaged over the pathlength, q, is described by the exponential depolarization equation, $$P = P_o e^{-2qx}$$

$P_o$ is the degree of polarization at $x=0$, P is the polarization at point x, and q is the average depolarization efficiency over the distance, x.

Although the publication Gian, P, et al., "Altitude-resolved Properties of a Saharian Dust Event over the Mediteranean," Atmospheric Environment, 34 5119-5127 (2000) (hereby incorporated by reference) did not report the degree of polarization P, the publication reported the depolarization coefficient that was measured, where D is defined as:

$$D = I_v / I_H$$

where $I_v$ and $I_H$ are the intensities of the horizontal polarization (that of the laser EMR) and vertical (cross polarization state of laser of the EMR). $I_v$ and $I_H$ are functions of path length from laser to scattering point in the atmosphere.

The relationship between experimental depolarization coefficient, D, and polarization, P, was derived and is shown below. The depolarization D cannot be analyzed with an exponential dependence because the polarization P has an exponential dependence. Equations for the definition of degree of polarization, and the depolarization equation and combined in the polarization to depolarization relationship.

$$P = \frac{D-1}{D+1}$$

$$D = \frac{P+1}{P-1}$$

The relationship between D and distance is found by substituting the definition of depolarization efficiency into the equation expressing D in terms of P, which results in $$D = \frac{\cosh(qx)}{\sinh(qx)}.$$

The average depolarization efficiency, q, can be calculated from the distance, x, and the depolarization coefficient, D. Once q is known, the degree of depolarization signal used in fluorescence polarization can be estimated under the same set of atmospheric conditions and laser wavelengths. Values of the functional dependence of depolarization, D, on the product of pathlength and depolarization efficiency, qx, of the round trip of backscattered EMR may be calculated as shown in FIG. 12.

Atmospheric Calculation Results

Calculations were done for fluorescence from the ground without atmosphere, depolarization of the atmosphere was calculated from published data, and the impact of the depolarization on remote fluorescence polarimetric imaging were calculated.

Atmospheric Depolarization Efficiency

The efficiency of depolarization, q, was calculated from the data for polarization coefficient, D, and distance, x, given by a published backscatter lidar study.

The functional dependence of depolarization, D, on qx of the round trip of backscattered EMR is shown in FIG. 12. The value of qx was calculated by us using the value of D at 14 km in equation relating D to qx. The depolarization measured was over a distance of 14 km) so that the total distance of the round trip is 28 km. Average values of q were calculated for the round trip, x=28 km, of EMR from the laser to the backscattering position and back to the detector near the laser. The day by day value of the depolarization coefficient for the experiment is shown in FIG. 12. The values of depolarization coefficient start out before a sand storm as 0.09 and increase to values over 0.28 during a sand storm. The authors of the experimental study in the publication Gian, P, et al., "Altitude-resolved Properties of a Saharian Dust Event over the Mediteranean," Atmospheric Environment, 34 5119-5127 (2000) attributed the small value of depolarization D (approx. <10%) as being caused by the preponderance of spherical particles, while the increase of D during the dust storm (40-50%) was attributed to the percentage of nonspherical particles.

Figure 8:
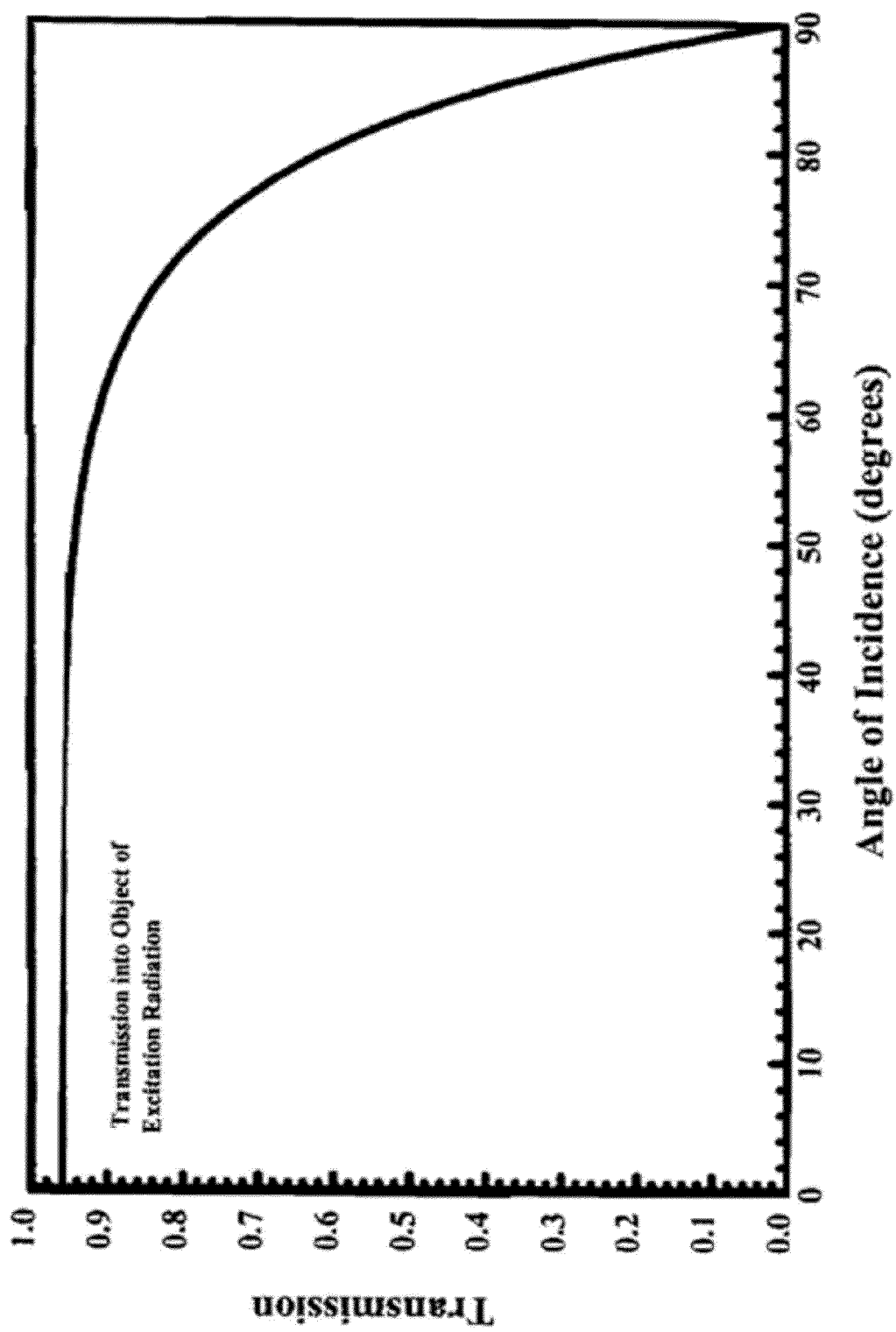
FIG. 8 is a graphical illustration of transmission versus angle of incidence for object of excitation radiation.

The depolarization efficiency from their data was calculated by us based upon our modeling of depolarization of the lidar backscatter. The results of the calculation are shown in FIG. 8 and in the particle shape table 1. The depolarization coefficient shown for the spherical particles is the average over the first 6 days, because they were before the storm where there was preponderance of spherical particles. The depolarization coefficient of the nonspherical particles was over 4 days at the peak of the storm (defined by hugest values) where nonspherical particles were predominant. The table of average polarization efficiency shows how these depolarization efficiency varied with particle shapes in their experiments.

TABLE 1

Average Depolarization Efficiency

| Particle Shape | Depolarization Efficiency | Sampling dates |
| --- | --- | --- |
| Spherical | $0.07 \pm 0.02$ km−1 | 6 May 1999 to 11 May 1999 |
| Nonspherical | $0.15 \pm 0.06$ km−1 | 18 May 1999 to 21 May 1999 |

The depolarization coefficient in a homogenous atmosphere gives a lower bound to the value of the depolarization efficiency of forward scattering. If the single backscattering event has a large depolarization associated with it) then the actual value of depolarization efficiency would be smaller. However, over large distances between object material and EMR source, the depolarization by forward scattering increases. So the depolarization coefficient is a measure of how much the atmosphere would interfere with differential polarization imaging over large distances. The small values of q may be related to the preponderance of spherical particles (i.e., water droplets) and the large values of q related to the nonspherical particles (i.e., dust). The depolarization efficiency, q, was calculated for each day before, during and after a dust storm from published backscatter lidar experiment.

The depolarization efficiency for each day is shown in FIG. 9. The backscatter coefficient was <0.1 for spherically symmetric and between 0.4 and 0.5 for spherically asymmetric particles. The inverse extinction coefficient was a few kilometers, and most of the extinction caused by scattering rather than absorptive processes. Polarization averaged distance, and for spherically asymmetric particles about 100% more than for spherical particles as shown in FIG. 9.

Atmospheric Calculation of Remote Fluorescence Polarimetry Signal

Figure 7:
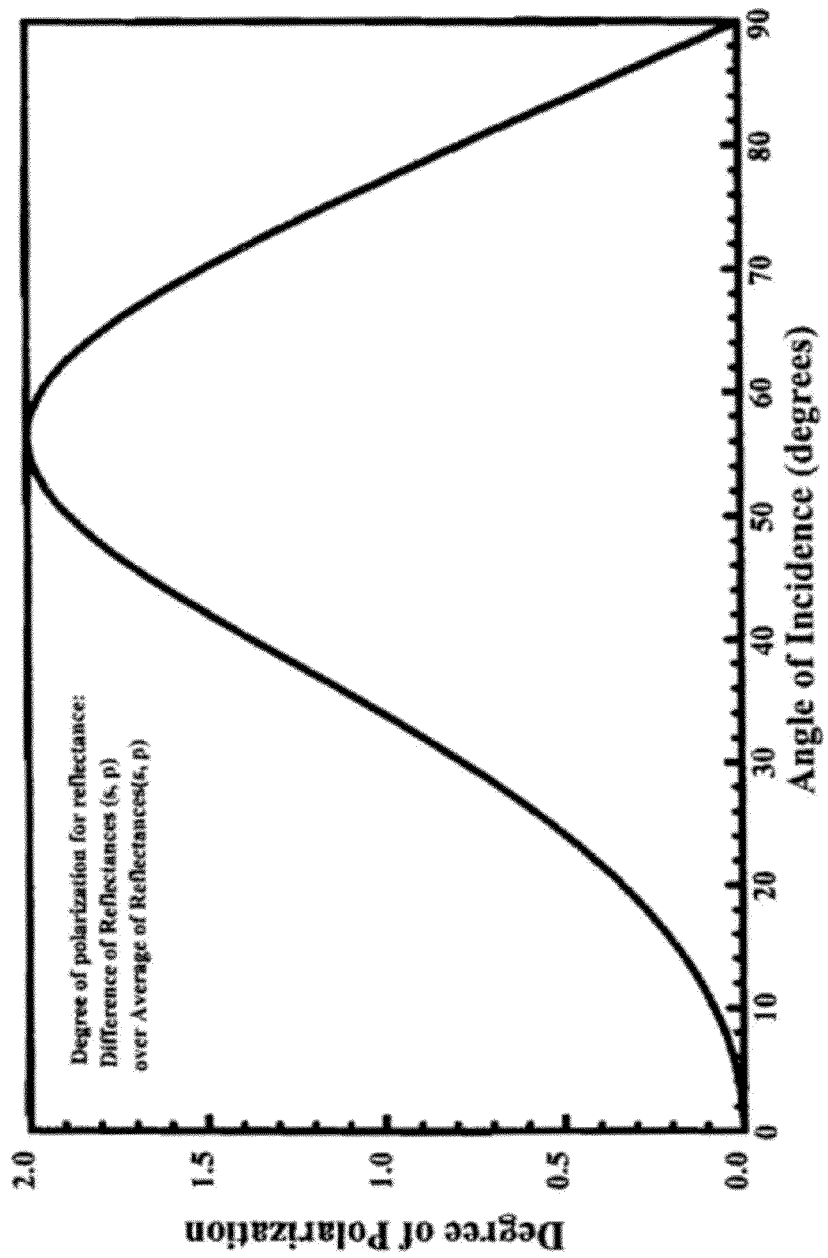
FIG. 7 is a graphical illustration of the degree of polarization as a function of incident angle by reflectance of s and p polarization states.

A scenario where a viewer is looking for dropped flat fluorescent plastic targets using fluorescence polarimetry was analyzed as follows. The viewer is either on a hill or in an aircraft at a height y above the ground as shown in FIG. 7. The viewer illuminates the flat ground, where the beam is at an angle θ to the zenith. The distance along the ground, x, was calculated by a standard trigonometric equation, the definition of tangent which is y=x tan θ and the distance, s, the beam must propagate through the atmosphere was calculated by the definition of cosine, which is s=x/cos θ.

The laser strikes the ground at an angle θ to the surface. The fluorescence is proportional to the Fresnel transmittance, where the index of refraction of the target is n=1.5. The signal strength given by the degree of polarization, P, at the object is shown as a function of horizontal distance, y, in FIG. 6 for q=0.15 km-1, given by the peak of the dust storm analyzed in the published study.

The degree of polarization of the laser beam at the target as measured by the fluorescence, was calculated using the equation for exponentially decaying degree of polarization and the definition of cosine. The degree of polarization, P, as a function of horizontal distance, y, is shown in FIG. 10 for three different values of height, x.

Calculations with Fresnel Equations. Calculations were done for nF=1.5 and nI=1 for showing how the differential polarization information persists through the diffuse reflection process, and how it has a functional dependence on the angle of incidence. The polarization-averaged specular reflectance, R, is shown as a function of incident angle, $\theta_I$, in FIG. 13 for nF=1.5. The polarization-averaged specular reflectance reaches its peak, which is I, near $\theta_I$=90° and stays nearly constant at 4% of the peak (i.e., R=0.04) for 0°<$\theta_I$<45°. The flat part of the curve, where the reflectance is at about 4%, is not sensitive to angle of incidence, and similarly is not sensitive to differential polarization.

Figure 6:
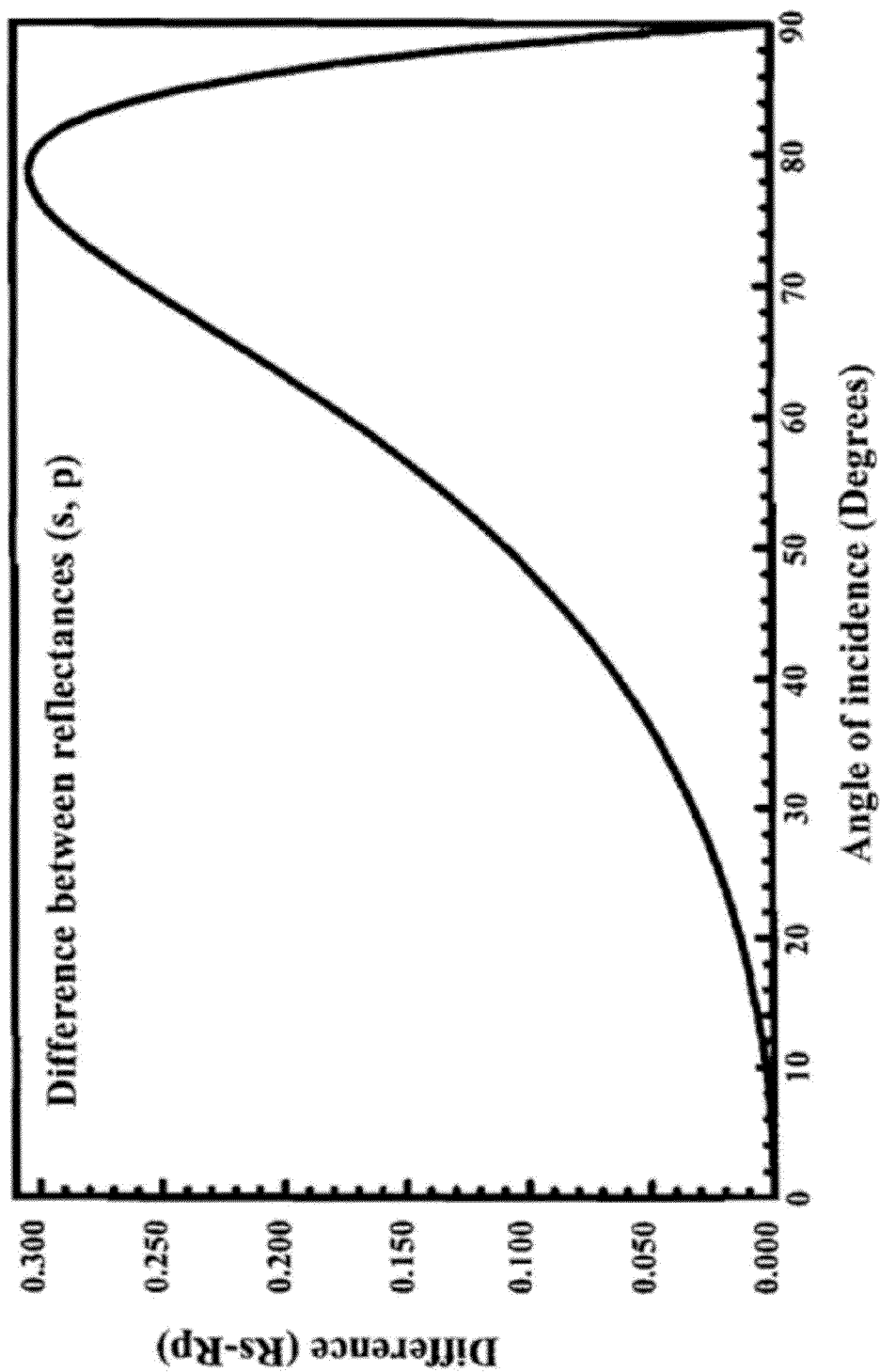
FIG. 6 is a graphical illustration depicting the difference between reflectances at two polarizations (s and p)

The differential polarization reflectance, ΔR, which is shown in FIG. 6 does not descend in value as rapidly as the polarization-averaged reflectance, R, which is shown in FIG. 13. The differential polarization reflectance reaches a peak of 0.3 at Brewster's angle, and is greater than 4% of this value for 10°<$\theta_I$<90°. There is no fiat portion to the curve, showing the differential polarization is sensitive to angle of incidence.

The degree of polarization, P, is shown in FIG. 7. This shows how strong the differential polarization signal is relative to the polarization average signal. The degree of polarization reaches a peak at Brewster's angle. The average transmission, T, through the surface is shown in FIG. 8.

A preferred embodiment provides a new method for detecting personnel in camouflaged or atmospherically obscured environments. The method uses time-varying differential polarization in laser EMR to excite fluorescence emission intensity, resulting in a fluorescent image that varies in time. The intensity of emission varies because the fluorescence emission is anticorrelated with specular reflectance that itself varies strongly with polarization. Signatures of personnel that this method detects include strongly fluorescing substances such as oil on skin, dyes on clothes, and surface features such as faces and outlines. The coupling between fluorescence and specular reflectance results in an image that will be more chemically specific than images acquired by nonpolarization methods, and less sensitive to atmospheric obscuration than fluorescence imaging excited by a source with constant polarization. If a scattering particle is in the atmosphere outside the object, the process is called atmospheric scattering. If an inhomogeneity inside the object, the process is called diffuse reflection.

The polarization-averaged reflectance, R, is a significant fraction of its peak only for a small range of angles ($80°<\theta_f<90°$). An object observed under this condition would look highly distorted, because only parts near the edge would not be distorted. However the differential polarization reflectance, $\Delta R$, is a significant fraction of the peak over a much large range of angle ($10°<\theta_f<89°$). Therefore, the entire object will be imaged with almost no distortion. If the EMR were scattered into the aperture, the differential reflectance image would be much easier to distinguish than the polarization-averaged reflectance image.

If one were to measure only the specular reflectance as a function of incident angle $\theta_f$, and use incident EMR that is unpolarized, the total specular reflection would display a degree of linear polarization proportional to P that is shown in FIG. 7. This polarization would be strongest for ($\theta_f=\theta_B$, where $\theta_B$ is Brewster's angle. The resulting image produced with polarization would be undistorted over a larger region than R but a smaller region than $\Delta R$. However, the background produced by atmospheric scattering would mask this image.

If the fluorescence intensity was used to produce an image, the image would be proportional to the average transmission shown in FIG. 8. However, atmospherically scattered EMR would produce a background. the incident EMR could vary in time and the differential reflectance measured. A filter in front of the camera would remove the scattered EMR but allow the emitted EMR through. Then the image would be as in FIG. 8 but without the background from scattered EMR.

The method introduced herein, using time varying differentially polarization to cause time varying fluorescence intensity, was investigated analytically and modeled. The method uses time-varying differential polarization in laser EMR to excite a time varying fluorescence emission intensity, resulting in a fluorescent image that varies in time. The intensity of emission varies because the fluorescence emission is anticorrelated with specular reflectance that itself varies strongly with polarization. Substances that strongly fluoresce include oil on skin, dyes on clothes, and other personnel signatures. Therefore, differential polarized reflectance detected using fluorescence may be useful for distinguishing the edges of objects that are masked by atmospheric scattering or blend into their surroundings. The measurement of differential reflectance with polarization may be useful for imaging through the atmosphere.

The methodologies described above permit, inter alia, detection of personnel in camouflaged, or atmospherically obscured environments including the detection of dropped fluorescent targets. Detection of concealed targets through a variety of airborne and ground based sensor efforts may be achieved. A new remote method of imaging to address these needs, using differential polarization and fluorescence is described and modeled for detecting personnel in camouflaged or atmospherically obscured environments. The impact of depolarization on remote fluorescence polarimetry was analyzed for a particular scenario. Depolarization efficiencies calculated from experimental data are shown. Non-spherical particles are shown to affect degree of polarization at target over a distance on the order of 14 km under certain conditions.

As used herein the terminology signal processing circuitry includes a computer, processor, microprocessor, multiprocessor, controller, mainframe, or a plurality of computers, processors, microprocessors, multiprocessors, controller, or mainframes or equivalents thereof.

As used herein, the terminology "object" may include a thing, a person, animate or inanimate subject, a plurality of objects, the ground, ground covering (e.g., grass), a localized piece or pieces of the environment, surface, physical entity (or entities) or anything that has photoemission.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

Patents, patent applications, or publications mentioned in this specification are incorporated herein by object to the same extent as if each individual document was specifically and individually indicated to be incorporated by object.

Having described the invention, the invention is now claimed.

The invention claimed is:

1. A system for investigating properties of an object comprising:
   a transmitter, including a radiation source, the transmitter providing incident radiation having a plurality of predetermined polarization states; the incident radiation illuminating an object and thereby causing the object to emit photoemission;
   a receiver, receiving photoemission from the object when the object is illuminated by the incident radiation, the receiver including a detector, the detector providing photoemission intensity data; and signal processing circuitry, in electrical communication with the detector, the signal processing circuitry determining three-dimensional information relating to the object from the photoemission intensity data for each of the plurality of incident polarization states.

2. The system of claim 1, wherein the incident radiation comprises a plurality of predetermined polarization states sequentially varied over time and wherein the object is remotely positioned relative to the apparatus and wherein the detector collects the photoemission intensity data from a single viewpoint and wherein the signal processing circuitry determines compositional information related to the object.

3. The system of claim 1, wherein the plurality of incident polarization states includes a first incident polarization state and a second incident polarization state, the object emitting photoemission at a first photoemission intensity when the incident radiation has a first polarization state and the object emitting photoemission at a second photoemission intensity when the incident radiation has a second polarization state; the signal processing circuitry calculating a difference between a first and second photoemission intensities; whereby three dimensional data is created based upon the photoemission intensities.

4. The system of claim 1 wherein the signal processing circuitry determines surface height profiles calculated by a polarimetric mathematical technique using images recorded at different times wherein a first image is recorded at a first polarization state of incident radiation, and a second image is recorded at a second polarization state of incident radiation, the brightness of each pixel corresponding to a point in the image increasing with the photoemission emission intensity, which carries information on the three-dimensional shape of the object based upon specular reflectance varying with incident angle as well as incident polarization and surface curvature and changes in angle of incidence are embedded in the object photoemission signal as the time variation of emission intensity.

5. The system of claim 3 wherein the signal processing circuitry determines surface height profiles calculated by polarimetric mathematical technique using images recorded at different times wherein a first image is recorded at a first polarization state of incident radiation, and a second image is recorded at a second polarization state of incident radiation, the brightness of each pixel corresponding to a point in the image increasing with the photoemission emission intensity, which carries information on the three-dimensional shape of the object based upon specular reflectance varying with incident angle as well as incident polarization and surface curvature and changes in angle of incidence are thus embedded in the object photoemission signal as the time variation of emission intensity.

6. The system of claim 1 wherein a plurality of images of the same object are derived from the different polarization states, the variation of polarization producing images wherein points on the object appear to move from one image relative to another due to differing photoemission intensity, where the apparent movement of the points can be represented by vectors which are used to produce a three dimensional image.

7. The system of claim 6 wherein the variation between images produced by varying the polarization is optical flow which results from taking an image of the same scene using different polarizations such that there is an apparent change of intensity from one image to another, such that a vector or vectors may be used to show the apparent movement.

8. The system of claim 7 wherein the optical flow at each image point x and y is calculated using two images of the same scene that can be described as brightness value matrices, the brightness element being defined so that its brightness is constant in wavelength and the rate that brightness changes with respect to wavelength is zero, such that $$\frac{dE(\vec{s})}{d\xi} = 0.$$

where E is, the brightness of the element at point $\vec{s} = x\hat{n}_x + y\hat{n}_y$ and the wavelength is $\xi$.

9. The system of claim 8 wherein the chain rule of differentiation is applied to the rate of changing brightness to derive a continuity condition from the chain rule by $$\frac{\partial E}{\partial x}\frac{dx}{d\xi} + \frac{\partial E}{\partial y}\frac{dy}{d\xi} + \frac{\partial E}{\partial \xi} = 0,$$

where the partial derivatives of the brightness are $$E_x = \frac{\partial E}{\partial x},$$

$$E_y = \frac{\partial E}{\partial y},$$

and $$E_\xi = \frac{\partial E}{\partial \xi}.$$

10. The system of claim 9 wherein the condition of continuity is a constraint necessary to specify a unique solution to the surface depth, but is insufficient to calculate a unique solution to the optical flow, and the perceived direction of optical flow is determined to be in the direction parallel to the gradient of brightness, and the optical flow component that is parallel to the brightness gradient in the xy-plane is designated as $D_{xy}$, where $$\vec{D}_{xy} = D_x\hat{n}_x + D_y\hat{n}_y,$$

then the continuity condition can be shown to be equivalent $$\vec{D}_{xy} = -\frac{E_\xi}{\sqrt{E_x^2 + E_y^2}}\hat{n}_{xy}$$

where $\hat{n}_{xy}$ is a normalized vector parallel to the gradient of brightness on the image (i.e., xy) plane.

11. The system of claim 10 wherein the surface depth value, which may be designated as z, is calculated for a perceived 3D object and the slopes of the surface depth on the perceived object are defined by p and q where:

$$p = -\frac{\partial z}{\partial x}$$

and $$q = -\frac{\partial z}{\partial y}.$$

such that the components p and q are proportional to $|D_x\hat{n}_x + D_y\hat{n}_y|$ which is the magnitude of the optical flow and the component of optical flow, D(arrow), that is perpendicular to the brightness gradient, E.

12. The system of claim 11 wherein the components p and q are proportional to $|D_x\hat{n}_x + D_y\hat{n}_y|$ which is the magnitude of the optical flow and the component of optical flow D(arrow), is perpendicular to the brightness gradient, E(arrow), is determined using a smoothness constraint, which limits the motion of the image in a way that the image can be visualized as sliding on the surface of the object being imaged, and wherein equations for optical flow can be solved such that E, $D_x$ and $D_y$ are digitized, and integer values are assigned to x, y, and $\xi$ so x→j, y→i, $\xi$→k where i, j, k=0, . . . , $N_{x,y,z}$ The local partial derivatives of $\vec{E}$ are averaged for a cube of adjacent values of i, j, and k by $$\overline{E}_x = \frac{1}{4}\{(E_{i,j+1,k} - E_{ijk}) + (E_{i+1,j+1,k} - E_{i+1,j,k}) +$$

$$(E_{i,j+1,k+1} - E_{i,j,k+1}) + (E_{i+1,j+1,k+1} - E_{i+1,j,k+1})\}$$

$$\overline{E}_y = \frac{1}{4}\{(E_{i+1,j,k} - E_{ijk}) + (E_{i+1,j+1,k} - E_{i,j+1,k}) +$$

$$(E_{i+1,j,k+1} - E_{i,j,k+1}) + (E_{i+1,j+1,k+1} - E_{i,j,k+1})\}$$

$$\overline{E}_\xi = \frac{1}{4}\{(E_{i,j,k+1} - E_{ijk}) + (E_{i+1,j,k+1} - E_{i+1,j,k}) +$$

$$(E_{i,j+1,k+1} - E_{i,j+1,k}) + (E_{i+1,j+1,k+1} - E_{i+1,j+1,k})\}$$

where $\overline{E}_x$, $\overline{E}_y$, and $\overline{E}_\xi$ are the average ties of $E_x$, $E_y$, and $E_\xi$, at a point designated by i, j, and k.

13. The system of claim 11 wherein optical flow, Dx and Dy, is calculated from the averaged derivatives by an iterative algorithm wherein the Dx and Dy are reassigned as u and v and $u^{(n)}$ and $v^{(n)}$ represent the calculated value for u and v at a point designated by integers I, j and k, where n designates a step of the iteration, then the (n+1) step is $$u^{(n+1)} = \bar{u}^{(n)} - \bar{E}_x[\bar{E}_x\bar{u}^{(n)} + \bar{E}_y\bar{u}^{(n)} + \bar{E}_\xi]/[\delta^2 + \bar{E}_x^2 + \bar{E}_y^2]$$

$$v^{(n+1)} = \bar{v}^{(n)} - \bar{E}_y[\bar{E}_x\bar{u}^{(n)} + \bar{E}_y\bar{u}^{(n)} + \bar{E}_\xi]/[\delta^2 + \bar{E}_x^2 + \bar{E}_y^2]$$

where $\bar{u}^{(n)}$ and $\bar{v}^{(n)}$ are the averaged values of the optical flow components at iteration n and $\delta^2$ is an input parameter less than or equal to $\bar{E}_x^2 + \bar{E}_y^2$, and the numerical parameter, $\delta^2$; partially compensates for computational noise in $\bar{E}_x$, $\bar{E}_y$, and $\bar{E}_\xi$, the input parameter, $\delta^2$, has a small value $(0 \leq \delta^2 \leq \bar{E}_x^2 + \bar{E}_y^2)$ that should be set at greatest accuracy to the anticipated noise value of $\bar{E}_x^2 + \bar{E}_y^2$, with convergence even for $\delta^2 = 0$, and the value of $u^{(n+1)}$ and $v^{(n+1)}$ do not directly depend on $u^{(n+1)}$ and $v^{(n+1)}$, but depends on their averaged local values $\bar{u}^{(n)}$ and $\tilde{u}^{(n)}$ calculated by the following weighted averaging formulas:

$$\bar{u}_{ijk}^{(n)} = \frac{1}{6}\{u_{i-1,j,k}^{(n)} + u_{i,j+1,k}^{(n)} + u_{i+1,j,k}^{(n)} + u_{i+1,j,k}^{(n)}\} + $$
$$\frac{1}{12}\{u_{i-1,j-1,k}^{(n)} + u_{i-1,j+1,k}^{(n)} + u_{i+1,j+1,k}^{(n)} + u_{i+1,j-1,k}^{(n)}\}$$

$$\bar{v}_{ijk}^{(n)} = \frac{1}{6}\{v_{i-1,j,k}^{(n)} + v_{i,j+1,k}^{(n)} + v_{i+1,j,k}^{(n)} + v_{i+1,j,k}^{(n)}\} + $$
$$\frac{1}{12}\{v_{i-1,j-1,k}^{(n)} + v_{i-1,j+1,k}^{(n)} + v_{i+1,j+1,k}^{(n)} + v_{i+1,j-1,k}^{(n)}\}$$

and wherein $E_{ijk}$ is, for each k, an $N^{i+1}+1$ by $N_{j+1}+1$ matrix (for i=0, 1, 2, 3, ... Ni and j=0, 1, 2, 3, ..., $N_j$), then the optical flow at each k is an $N_i$ by $N_j$ matrix, and the initial values (n=0) of the optical flow components can be chosen as zero, $$\bar{u}_{ijk}^{(0)} = \bar{v}_{ijk}^{(0)} = 0$$

and the constants ⅙ and 1/12 are chosen to optimize convergence using a cube of local values determined by the two images at different wavelengths designated by integers k and k+1.

14. The system of claim 1, wherein the receiver receives photoemission data in the form of an image and the receiver determines optical flow data from a plurality of photoemission images of the object, and determines the three-dimensional data from the optical flow data, and wherein the receiver is a camera and the photoemission intensity data is collected from a single viewpoint and wherein each image taken by the camera produced by the photoemission corresponds to a two-dimensional image of the object; and wherein the images taken by the camera vary depending upon the polarization state of the incident radiation which produces differing photoemission, the changes in the images being processed so as to create three dimensional data and wherein the at least one processor comprises computer signal processing circuitry operatively associated with the polarization modulator and the receiver, the signal processing circuitry correlating the photoemission intensity data with the time-dependent initial polarization of the incident radiation.

15. The apparatus of claim 1, wherein the transmitter further comprises a polarization modulator.

16. The apparatus of claim 1, wherein the radiation source is a pulsed laser and wherein the receiver further comprises a filter, the filter selectively transmitting photoemission radiation from the object.

17. The apparatus of claim 1, wherein the receiver is a spectrometer providing photoemission compositional spectra of the object.

18. A method of determining three-dimensional information relating to an object by monocular polarimetric imaging, the method comprising:
providing incident radiation, the incident radiation having a time-dependent polarization including a plurality of initial polarization states;
illuminating the object with the incident radiation;
receiving photoemission from the object;
determining photoemission intensity data relating to the object for four or more initial polarization states; and
determining the three-dimensional information relating to the object from the photoemission intensity data.

19. The method of claim 18, wherein the three-dimensional information is a surface profile of the object, and wherein the three-dimensional information are derived from the angles θ and φ of the normal vector to the object surface, and wherein the photoemission intensity data is determined from a first photoemission intensity at a first initial polarization state of excitation, and a second photoemission intensity at a second initial polarization state of excitation.

20. The method of claim 18, wherein the photoemission intensity data includes an intensity difference between the first photoemission intensity and the second photoemission intensity and wherein receiving photoemission from the object includes determining a plurality of photoemission intensity images of the object corresponding to each of the plurality of polarization states.

21. The method of claim 18, wherein determining the three-dimensional information comprises calculating optical flow data using the plurality of polarimetric images, the three-dimensional information being determined from the optical flow data and wherein the method further comprises collection of a photoemission compositional spectrum using a spectral library of known compositions from the object along with the three-dimensional information.

* * * * *